United States Patent
Heinrikson et al.

(10) Patent No.: US 6,387,643 B1
(45) Date of Patent: *May 14, 2002

(54) HUMAN PLATELET HEPARANASE POLYPEPTIDES, POLYNUCLEOTIDE MOLECULES THAT ENCODE THEM, AND METHODS FOR THE IDENTIFICATION OF COMPOUNDS THAT ALTER HEPARANASE ACTIVITY

(75) Inventors: Robert Leroy Heinrikson, Plainwell; Michael B. Fairbanks; Ana M. Mildner, both of Kalamazoo, all of MI (US)

(73) Assignee: Pharmacia and Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,586

(22) Filed: Feb. 18, 1999

Related U.S. Application Data

(60) Provisional application No. 60/075,706, filed on Feb. 24, 1998, and provisional application No. 60/079,401, filed on Mar. 26, 1998.

(51) Int. Cl.$^7$ .............................. C12Q 1/34; C12N 9/00; C07K 1/00
(52) U.S. Cl. .............................. 435/18; 435/4; 435/183; 435/195; 435/200; 435/201; 530/350
(58) Field of Search ................................ 530/350, 395, 530/402; 435/18, 69.1, 209, 4, 200, 195, 183, 201; 536/23.1, 23.5; 424/94.61, 94.6, 94.1

(56) References Cited

U.S. PATENT DOCUMENTS

| | | |
|---|---|---|
| 4,882,318 A | 11/1989 | Vlodavsky et al. |
| 5,362,641 A | 11/1994 | Fuks et al. |
| 5,567,417 A | 10/1996 | Saisekharan et al. |
| 5,968,822 A * | 10/1999 | Pecker et al. ................ 435/325 |

FOREIGN PATENT DOCUMENTS

| | | |
|---|---|---|
| WO | WO 91/02977 | 3/1991 |
| WO | WO 95/04158 | 7/1994 |
| WO | WO 97/11684 | 9/1996 |
| WO | WO 98/03638 | 7/1997 |
| WO | WO 99/11798 | 8/1998 |
| WO | WO 99/40207 | 8/1999 |

OTHER PUBLICATIONS

L.E. Freed, G.V. Vunjak–Novakovic, H. Bernstein, C.L. Conney, R. Langer "Kinetics of Immobilized Heparinase in Human Blood," Ann. Biomed. Eng., 1993, 21:67–76.

R Fridman, O Lider, Y Naparstek, Z Fuks, I Vlodavsky, IR Cohen, "Soluble Antigen Induces T Lymphocytes to Secrete an Endoglycosidase That Degrades the Heparan Sulfate Moiety of Subendothelial Extracellular Matrix," J. Cell. Physiol., 1987, 130: 85–92.

K Godder, I Vlodavsky, A Eldor, BB Weksler, A Haimovitz–Freidman, "Heparanase Activity in Cultured Endothelial Cells," J. Cell Physiol., 1991,148:274–280.

R Goshen, AA Hochberg, G Korner, E Levy, R Ishai–Michaeli, M Elkin, N DeGroot, I Vlodavsky, "Purification and characterization of placental heparanase and its expression by cultured cytotrophoblasts," Molecular Human Reproduction, vol. 2 No. 9: 679–684, 1996, XP–002106141.

A Haimovitz–Friedman, DJ Falcone, A Eldor, V Schirrmacher, I Vlodavsky, Z Fuks, "Activation of Platelet Heparitinase by Tumor Cell–Derived Factors," Blood, 1991,78:789–796.

L Hillier, N Clark, T Dubuque, K Elliston, M Hawkins, M Holman, M Hultman, T Kucaba, M Le, G Lennon, M Marra, J Parsons, L Rifkin, T Rohlfing, M Soares, F Tan, E Trevaskis, R Waterston, A Williamson, P Wohldmann, R Wilson, "The WashU–Merck EST Project," Unpublished, Sequence 587 BP, XP–002115496.

AJ Hoogewerf, J Leone, I Reardon, RL Heinrikson, SR Ledbetter, "Isolation of human platelet heparanase: Identity with connective tissue activating peptide (CTAP–III)," Abstract No. 1657, XP–002115494.

L Jin, "The molecular cloning and characterization of human heparanase cDNA and the immunochemical localization of heparanase in metastatic melanomas," The Univ. of Texas H.S.C. at Houston Grad. Sch. of Biomed. Sci., 1992, 124pp, XP–002115493.

L Jin, M Nakajima, GL Nicolson, "Immunochemical Localization of Heparanase in Mouse and Human Melanomas" International Journal of Cancer, 45: 1088–1095, 1990, XP–002115495.

L Jin, M Nakajima, GL Nicolson, "Molecular cloning and expression of human heparanase cDNA," Abstract No. 343, XP–002115492.

My Khan, SA Newman, "A Rapid Colorimetric Assay for Heparinase Activity," Anal. Biochem., 1991, 196:373–376.

U Klein, K von Figura, "Partial Purification and Characterization of a Heparan Sulfate Specific Endoglucuronidase," BBRC, 1976, vol. 73 No. 3:569–576.

(List continued on next page.)

Primary Examiner—Sean McGarry
Assistant Examiner—Janet Epps
(74) Attorney, Agent, or Firm—Edward F. Rehberg; Lori E. Kerber

(57) ABSTRACT

The present invention provides isolated human heparanase polypeptides, and the isolated polynucleotide molecules that encode them, as well as vectors and host cells comprising such polynucleotide molecules. The invention also provides a method for the identification of an agent that alters heparanase activity.

10 Claims, 10 Drawing Sheets

OTHER PUBLICATIONS

M. Kosir, C. Quinn, K. Zukowski, D. Grignon, S. Ledbetter, "Human Prostate Carcinoma Cells Produce Extracellular Heparanase," J. Surg. Res., 1997, 67:98–105.

Y Matzner, I Vlodavsky, M Bar–Ner, R Ishai–Michaeli, AI Tauber, "Subcellular localization of heparanase in human neutrophils," 1992, 51:519–524.

M Nakajima, T Irimura, GL Nicolson, "A Solid–Phase Substrate of Heparanase: Its Application to Assay of Human Melanoma for Heparan Sulfate Degradative Activity," Anal. Biochem., 1986, 157:162–171.

M Nakajima, T Irimura, GL Nicolson, "Tumor Metastasis–Associated Heparanase (Heparaan Sulfate Endoglycosidase) Acitivity in Human Melanoma Cells," Cancer Letters, 1986, 31:277–283.

S. Ögren, U Lindahl, "Cleavage of Macromolecular Heparin by an Enzyme from Mouse Mastocytoma," J. Biol. Chem., 1975, 250:2690–2697.

CR Parish, DR Coombe, KB Jakobsen, FA Bennett, PA Underwood, "Evidence that Sulphated Polysaccharides Inhibit Tumour Metastasis by Blocking Tumour–Cell–Derived Heparanases," Int. J. Cancer, 1987, 40:511–518.

AC Rapraeger, A Krufka, BB Olwin, "Requirement of Heparan Sulfate for bFGF–Mediated Fibroblast Growth and Myoblast Differentiation," Science, 1991, 252:1705–1708.

RF Sewell, PEC Brenchley, NP Mallick, "Human mononuclear cells contain an endoglycosidase specific for heparan sulphate glycosaminoglycan demonstrable with the use of a specific solid–phase metabolically radiolabelled substrate," Biochem. J., 1989, 264:777–783.

U Vettel, R Bar–Shavit, MM Simon, G Brunner, I Vlodavsky, MD Kramer, "Coordinate secretion and functional synergism of T cell–associated serine proteinase–1 (MTSP–1) and endoglycosidase(s) of activated T cells," Eur. J. Immunol., 1991, 21:2247–2251.

I Vlodavski, A Eldor, A Haimovitz–Friedman, Y Matzner, R Ishai–Michaeli, O Lider, Y Naparstek, IR Cohen, Z Fuks, "Expression of Heparanase by Platelets and Circulating Cells of the Immune System: Possible Involvement in Diapedesis and Extravasation," Invasion Metastasis, 1992, 12:112–127.

J. Yahalom, E. Fibach, R. Bar–Tana, Z. Fuks, I. Vlodavsky, "Differentiating Human–Leukemia Cells Express Heparanase that Degrades Heparan Sulfate in Subendothelial Extracellular Matrix," Leukemia Research, 1988, 12:711–717.

* cited by examiner

```
                                                     1                   7
                                                     M   L   L   L   G   P
                                                     ATGCTGCTGCTCCTGGGGC
                                                     1                  19

8                                                                 27
      L   G   P   F   S   P   G   A   L   P   R   P   A   Q   A   Q   D   V   V   D
      CGCTGGGTCCCTTCTCCCCTGGCGCCTTGCCCCGACCTGCGCAAGCACAGGACGTCGTGG
     20                                                                 79

28                                                                 47
      L   D   F   F   T   Q   E   P   L   H   L   V   S   P   S   F   L   S   V   T
      ACCTGGACTTCTTCACCCAGGAGCCGCTGCACCTGGTGAGCCCCTCGTTCCTGTCCGTCA
     80                                                                139

48                                                                 67
      I   D   A   N   L   A   T   D   P   R   F   L   I   L   L   G   S   P   K   L
      CCATTGACGCCAACCTGGCCACGGACCCGCGGTTCCTCATCCTCCTGGGTTCTCCAAAGC
    140                                                                199

68                                                                 87
      R   T   L   A   R   G   L   S   P   A   Y   L   R   F   G   G   T   K   T   D
      TTCGTACCTTGGCCAGAGGCTTGTCTCCTGCGTACCTGAGGTTTGGTGGCACCAAGACAG
    200                                                                259

88                                                                107
      F   L   I   F   D   P   K   K   E   S   T   F   E   E   R   S   Y   W   Q   S
      ACTTCCTAATTTTCGATCCCAAGAAGGAATCAACCTTTGAAGAGAGAAGTTACTGGCAAT
    260                                                                319

108                                                                127
      Q   V   N   Q   D   I   C   K   Y   G   S   I   P   P   D   V   E   E   K   L
      CTCAAGTCAACCAGGATATTTGCAAATATGGATCCATCCCTCCTGATGTGGAGGAGAAGT
    320                                                                379

128                                                                147
      R   L   E   W   P   Y   Q   E   Q   L   L   L   R   E   H   Y   Q   K   K   F
      TACGGTTGGAATGGCCCTACCAGGAGCAATTGCTACTCCGAGAACACTACCAGAAAAAGT
    380                                                                439

148                                                                167
      K   N   S   T   Y   S   R   S   S   V   D   V   L   Y   T   F   A   N   C   S
      TCAAGAACAGCACCTACTCAAGAAGCTCTGTAGATGTGCTATACACTTTTGCAAACTGCT
    440                                                                499
```

FIGURE 7B

```
       168                                                                   187
          G   L   D   L   I   F   G   L   N   A   L   L   R   T   A   D   L   Q   W   N
       CAGGACTGGACTTGATCTTTGGCCTAAATGCGTTATTAAGAACAGCAGATTTGCAGTGGA
500                                                                          559
       188                                                                   207
          S   S   N   A   Q   L   L   L   D   Y   C   S   S   K   G   Y   N   I   S   W
       ACAGTTCTAATGCTCAGTTGCTCCTGGACTACTGCTCTTCCAAGGGGTATAACATTTCTT
560                                                                          619

208                                                                   227
          E   L   G   N   E   P   N   S   F   L   K   K   A   D   I   F   I   N   G   S
       GGGAACTAGGCAATGAACCTAACAGTTTCCTTAAGAAGGCTGATATTTTCATCAATGGGT
620                                                                          679

228                                                                   247
          Q   L   G   E   D   F   I   Q   L   H   K   L   L   R   K   S   T   F   K   N
       CGCAGTTAGGAGAAGATTTTATTCAATTGCATAAACTTCTAAGAAAGTCCACCTTCAAAA
680                                                                          739

248                                                                   267
          A   K   L   Y   G   P   D   V   G   Q   P   R   R   K   T   A   K   M   L   K
       ATGCAAAACTCTATGGTCCTGATGTTGGTCAGCCTCGAAGAAAGACGGCTAAGATGCTGA
740                                                                          799

268                                                                   287
          S   F   L   K   A   G   G   E   V   I   D   S   V   T   W   H   H   Y   Y   L
       AGAGCTTCCTGAAGGCTGGTGGAGAAGTGATTGATTCAGTTACATGGCATCACTACTATT
800                                                                          859

288                                                                   307
          N   G   R   T   A   T   K   E   D   F   L   N   P   D   V   L   D   I   F   I
       TGAATGGACGGACTGCTACCAAGGAAGATTTTCTAAACCCTGATGTATTGGACATTTTTA
860                                                                          919

308                                                                   327
          S   S   V   Q   K   V   F   Q   V   V   E   S   T   R   P   G   K   K   V   W
       TTTCATCTGTGCAAAAAGTTTTCCAGGTGGTTGAGAGCACCAGGCCTGGCAAGAAGGTCT
920                                                                          979

328                                                                   347
          L   G   E   T   S   S   A   Y   G   G   A   P   L   L   S   D   T   F   A
       GGTTAGGAGAAACAAGCTCTGCATATGGAGGCGGAGCGCCCTTGCTATCCGACACCTTTG
980                                                                         1039

348                                                                   367
          A   G   F   M   W   L   D   K   L   G   L   S   A   R   M   G   I   E   V   V
       CAGCTGGCTTTATGTGGCTGGATAAATTGGGCCTGTCAGCCCGAATGGGAATAGAAGTGG
1040                                                                        1099
```

FIGURE 7C

```
       368                                                      387
         M   R   Q   V   F   F   G   A   G   N   Y   H   L   V   D   E   N   F   D   P
       TGATGAGGCAAGTATTCTTTGGAGCAGGAAACTACCATTTAGTGGATGAAAACTTCGATC
1100                                                                        1159

388                                                      407
         L   P   D   Y   W   L   S   L   L   F   K   K   L   V   G   T   K   V   L   M
       CTTTACCTGATTATTGGCTATCTCTTCTGTTCAAGAAATTGGTGGGCACCAAGGTGTTAA
1160                                                                        1219

408                                                      427
         A   S   V   Q   G   S   K   R   R   K   L   R   V   Y   L   H   C   T   N   T
       TGGCAAGCGTGCAAGGTTCAAAGAGAAGGAAGCTTCGAGTATACCTTCATTGCACAAACA
1220                                                                        1279

428                                                      447
         D   N   P   R   Y   K   E   G   D   L   T   L   Y   A   I   N   L   H   N   V
       CTGACAATCCAAGGTATAAAGAAGGAGATTTAACTCTGTATGCCATAAACCTCCATAATG
1280                                                                        1339

448                                                      467
         T   K   Y   L   R   L   P   Y   P   F   S   N   K   Q   V   D   K   Y   L   L
       TCACCAAGTACTTGCGGTTACCCTATCCTTTTTCTAACAAGCAAGTGGATAAATACCTTC
1340                                                                        1399

468                                                      487
         R   P   L   G   P   H   G   L   L   S   K   S   V   Q   L   N   G   L   T   L
       TAAGACCTTTGGGACCTCATGGATTACTTTCCAAATCTGTCCAACTCAATGGTCTAACTC
1400                                                                        1459

488                                                      507
         K   M   V   D   D   Q   T   L   P   P   L   M   E   K   P   L   R   P   G   S
       TAAAGATGGTGGATGATCAAACCTTGCCACCTTTAATGGAAAAACCTCTCCGGCCAGGAA
1460                                                                        1519

508                                                      527
         S   L   G   L   P   A   F   S   Y   S   F   F   V   I   R   N   A   K   V   A
       GTTCACTGGGCTTGCCAGCTTTCTCATATAGTTTTTTTGTGATAAGAAATGCCAAAGTTG
1520                                                                        1579

528     530
         A   C   I   *
       CTGCTTGCATCTGA
```

FIGURE 8

(1)  $D_{24}$VVDLDFFTQEPLHLVSPSPLSV$_{46}$     PCAase Treated 8 kDa peptide (2)  $P_{76}$ RFLILLGSPKLRTFARGLSPAYLRFGGTKTD $_{87}$ CNBr Peptide (3)  $T_{86}$ DFLIFDPK$_{94}$     Tryptic Peptide (4)  $K_{146}$FKNSTYSRSSVDVLYTFANCSGLDLIF $_{172}$     EndoLysC Peptide (5)  $T_{181}$ADLQWNSSNAQLLLDYCSSK $_{201}$     Tryptic Peptide (6)  $G_{202}$YNISWELGNEPNSFLK$_{218}$    EndoLysC Peptide (7)  $K_{219}$ADIFINGSQLGEDFIQLHK$_{238}$    EndoLysC Peptide (8)  $L_{250}$YGPDVGQPR$_{260}$    Tryptic Peptide (9)  $A_{272}$GGEVIDSVTW$_{282}$    EndoLysC Peptide

(10) $E_{295}$ DFLNPDVLDIFISSVQK$_{312}$    Trptic Peptide

(11) $V_{313}$FQVVESTRPGK$_{324}$    Tryptic Peptide

(12) $V_{326}$WLGETSSAYGGA$_{339}$    Tryptic Peptide

(13) $R_{369}$QVFFGAGNYHLVDENFDPLPDYWLSLLFKKLVGTKVL $_{406}$ CNBr Frag

(14) $Y_{432}$KEGDLTLYAINLHNVTK$_{449}$    Tryptic Peptide

(15) $S_{479}$VQLNGLTLK$_{488}$    Tryptic Peptide

(16) $P_{502}$LRPGSSLGLPAFSYSFFVIRNAK$_{525}$    EndoLysC Peptide

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
       (A) LENGTH: 1593 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

| | | | | | |
|---|---|---|---|---|---|
| ATGCTGCTGC | TCCTGGGGCC | GCTGGGTCCC | TTCTCCCCTG | GCGCCTTGCC | CCGACCTGCG | 60 |
| CAAGCACAGG | ACGTCGTGGA | CCTGGACTTC | TTCACCCAGG | AGCCGCTGCA | CCTGGTGAGC | 120 |
| CCCTCGTTCC | TGTCCGTCAC | CATTGACGCC | AACCTGGCCA | CGGACCCGCG | GTTCCTCATC | 180 |
| CTCCTGGGTT | CTCCAAAGCT | TCGTACCTTG | GCCAGAGGCT | TGTCTCCTGC | GTACCTGAGG | 240 |
| TTTGGTGGCA | CCAAGACAGA | CTTCCTAATT | TTCGATCCCA | AGAAGGAATC | AACCTTTGAA | 300 |
| GAGAGAAGTT | ACTGGCAATC | TCAAGTCAAC | CAGGATATTT | GCAAATATGG | ATCCATCCCT | 360 |
| CCTGATGTGG | AGGAGAAGTT | ACGGTTGGAA | TGGCCCTACC | AGGAGCAATT | GCTACTCCGA | 420 |
| GAACACTACC | AGAAAAAGTT | CAAGAACAGC | ACCTACTCAA | GAAGCTCTGT | AGATGTGCTA | 480 |
| TACACTTTTG | CAAACTGCTC | AGGACTGGAC | TTGATCTTTG | GCCTAAATGC | GTTATTAAGA | 540 |
| ACAGCAGATT | TGCAGTGGAA | CAGTTCTAAT | GCTCAGTTGC | TCCTGGACTA | CTGCTCTTCC | 600 |
| AAGGGGTATA | ACATTTCTTG | GGAACTAGGC | AATGAACCTA | ACAGTTTCCT | TAAGAAGGCT | 660 |
| GATATTTTCA | TCAATGGGTC | GCAGTTAGGA | GAAGATTTTA | TTCAATTGCA | TAAACTTCTA | 720 |
| AGAAAGTCCA | CCTTCAAAAA | TGCAAAACTC | TATGGTCCTG | ATGTTGGTCA | GCCTCGAAGA | 780 |
| AAGACGGCTA | AGATGCTGAA | GAGCTTCCTG | AAGGCTGGTG | GAGAAGTGAT | TGATTCAGTT | 840 |
| ACATGGCATC | ACTACTATTT | GAATGGACGG | ACTGCTACCA | AGGAAGATTT | TCTAAACCCT | 900 |
| GATGTATTGG | ACATTTTTAT | TTCATCTGTG | CAAAAAGTTT | TCCAGGTGGT | TGAGAGCACC | 960 |
| AGGCCTGGCA | AGAAGGTCTG | GTTAGGAGAA | ACAAGCTCTG | CATATGGAGG | CGGAGCGCCC | 1020 |
| TTGCTATCCG | ACACCTTTGC | AGCTGGCTTT | ATGTGGCTGG | ATAAATTGGG | CCTGTCAGCC | 1080 |
| CGAATGGGAA | TAGAAGTGGT | GATGAGGCAA | GTATTCTTTG | GAGCAGGAAA | CTACCATTTA | 1140 |
| GTGGATGAAA | ACTTCGATCC | TTTACCTGAT | TATTGGCTAT | CTCTTCTGTT | CAAGAAATTG | 1200 |
| GTGGGCACCA | AGGTGTTAAT | GGCAAGCGTG | CAAGGTTCAA | AGAGAAGGAA | GCTTCGAGTA | 1260 |
| TACCTTCATT | GCACAAACAC | TGACAATCCA | AGGTATAAAG | AAGGAGATTT | AACTCTGTAT | 1320 |
| GCCATAAACC | TCCATAATGT | CACCAAGTAC | TTGCGGTTAC | CCTATCCTTT | TTCTAACAAG | 1380 |
| CAAGTGGATA | AATACCTTCT | AAGACCTTTG | GGACCTCATG | GATTACTTTC | CAAATCTGTC | 1440 |
| CAACTCAATG | GTCTAACTCT | AAAGATGGTG | GATGATCAAA | CCTTGCCACC | TTTAATGGAA | 1500 |
| AAACCTCTCC | GGCCAGGAAG | TTCACTGGGC | TTGCCAGCTT | TCTCATATAG | TTTTTTTGTG | 1560 |
| ATAAGAAATG | CCAAAGTTGC | TGCTTGCATC | TGA | | | 1593 |

-continued (2) INFORMATION FOR SEQ ID NO:2:

(i) SEQUENCE CHARACTERISTICS:
        (A) LENGTH: 530 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:2:

```
Met Leu Leu Leu Leu Gly Pro Leu Gly Pro Phe Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Arg Ser Ser Val Asp Val Leu
145                 150                 155                 160

Tyr Thr Phe Ala Asn Cys Ser Gly Leu Asp Leu Ile Phe Gly Leu Asn
                165                 170                 175

Ala Leu Leu Arg Thr Ala Asp Leu Gln Trp Asn Ser Ser Asn Ala Gln
            180                 185                 190

Leu Leu Leu Asp Tyr Cys Ser Ser Lys Gly Tyr Asn Ile Ser Trp Glu
        195                 200                 205

Leu Gly Asn Glu Pro Asn Ser Phe Leu Lys Lys Ala Asp Ile Phe Ile
    210                 215                 220

Asn Gly Ser Gln Leu Gly Glu Asp Phe Ile Gln Leu His Lys Leu Leu
225                 230                 235                 240

Arg Lys Ser Thr Phe Lys Asn Ala Lys Leu Tyr Gly Pro Asp Val Gly
                245                 250                 255

Gln Pro Arg Arg Lys Thr Ala Lys Met Leu Lys Ser Phe Leu Lys Ala
            260                 265                 270

Gly Gly Glu Val Ile Asp Ser Val Thr Trp His His Tyr Tyr Leu Asn
        275                 280                 285

Gly Arg Thr Ala Thr Lys Glu Asp Phe Leu Asn Pro Asp Val Leu Asp
    290                 295                 300

Ile Phe Ile Ser Ser Val Gln Lys Val Phe Gln Val Val Glu Ser Thr
305                 310                 315                 320

Arg Pro Gly Lys Lys Val Trp Leu Gly Glu Thr Ser Ser Ala Tyr Gly
                325                 330                 335

Gly Gly Ala Pro Leu Leu Ser Asp Thr Phe Ala Ala Gly Phe Met Trp
            340                 345                 350
```

```
Leu Asp Lys Leu Gly Leu Ser Ala Arg Met Gly Ile Glu Val Val Met
        355                 360                 365

Arg Gln Val Phe Phe Gly Ala Gly Asn Tyr His Leu Val Asp Glu Asn
        370                 375             380

Phe Asp Pro Leu Pro Asp Tyr Trp Leu Ser Leu Leu Phe Lys Lys Leu
385                 390                 395                 400

Val Gly Thr Lys Val Leu Met Ala Ser Val Gln Gly Ser Lys Arg Arg
                405                 410                 415

Lys Leu Arg Val Tyr Leu His Cys Thr Asn Thr Asp Asn Pro Arg Tyr
                420                 425             430

Lys Glu Gly Asp Leu Thr Leu Tyr Ala Ile Asn Leu His Asn Val Thr
            435                 440                 445

Lys Tyr Leu Arg Leu Pro Tyr Pro Phe Ser Asn Lys Gln Val Asp Lys
        450                 455                 460

Tyr Leu Leu Arg Pro Leu Gly Pro His Gly Leu Leu Ser Lys Ser Val
465                 470                 475                 480

Gln Leu Asn Gly Leu Thr Leu Lys Met Val Asp Asp Gln Thr Leu Pro
                485                 490                 495

Pro Leu Met Glu Lys Pro Leu Arg Pro Gly Ser Ser Leu Gly Leu Pro
            500                 505                 510

Ala Phe Ser Tyr Ser Phe Phe Val Ile Arg Asn Ala Lys Val Ala Ala
        515                 520                 525

Cys Ile
    530

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

CCGCCTCCAT ATGCAGAGCT                                              20

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

GGCTACAAGC TTGAAAAAGT TCAAGAACAG CACCTACTCA                         40
```

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GGCTGCTCGA GCGATGCAAG CAGCAACTTT GGC        33

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

GAAGGAAGCT GCGAGTATAC C        21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

GGTATACTCG CAGCTTCCTT CC        22

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GGCTATCTAG ACTGATGCTG CTGCTCCTGG        30

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

GGTCTGTCGA CTCAGATGCA AGCAGCAACT T                           31

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

GGATCATATG CAAAAAGTTC AAGAACAGCA CCTAC                     35

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

GGCTCGGTAC CTCAGATGCA AGCAGCAACT TTGGC                     35

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

AGCTCTGCAT ACGGAGGCGG A                                    21

```
(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

TCCGCCTCCG TATGCAGAGC T                                              21

(2) INFORMATION FOR SEQ ID NO:14:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:14:

Asp Val Val Asp Leu Asp Phe Phe Thr Gln Glu Pro Leu His Leu Val
1               5                  10                  15

Ser Pro Ser Pro Leu Ser Val
            20

(2) INFORMATION FOR SEQ ID NO:15:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:15:

Pro Arg Phe Leu Ile Leu Leu Gly Ser Pro Lys Leu Arg Thr Phe Ala
1               5                  10                  15

Arg Gly Leu Ser Pro Ala Tyr Leu Arg Phe Gly Gly Thr Lys Thr Asp
            20                  25                  30

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:16:

Thr Asp Phe Leu Ile Phe Asp Pro Lys
1               5
```

(2) INFORMATION FOR SEQ ID NO:17:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:17:

```
Lys Phe Lys Asn Ser Thr Tyr Ser Arg Ser Ser Val Asp Val Leu Tyr
1               5                   10                  15
Thr Phe Ala Asn Cys Ser Gly Leu Asp Leu Ile Phe
            20                  25
```

(2) INFORMATION FOR SEQ ID NO:18:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:18:

```
Thr Ala Asp Leu Gln Trp Asn Ser Ser Asn Ala Gln Leu Leu Leu Asp
1               5                   10                  15
Tyr Cys Ser Ser Lys
            20
```

(2) INFORMATION FOR SEQ ID NO:19:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:19:

```
Gly Tyr Asn Ile Ser Trp Glu Leu Gly Asn Glu Pro Asn Ser Phe Leu
1               5                   10                  15
Lys
```

(2) INFORMATION FOR SEQ ID NO:20:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:20:

```
Lys Ala Asp Ile Phe Ile Asn Gly Ser Gln Leu Gly Glu Asp Phe Ile
1               5                   10                  15
Gln Leu His Lys
            20
```

(2) INFORMATION FOR SEQ ID NO:21:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:21:

Leu Tyr Gly Pro Asp Val Gly Gln Pro Arg
1               5                   10

(2) INFORMATION FOR SEQ ID NO:22:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:22:

Ala Gly Gly Glu Val Ile Asp Ser Val Thr Trp
1               5                   10

(2) INFORMATION FOR SEQ ID NO:23:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:23:

Glu Asp Phe Leu Asn Pro Asp Val Leu Asp Ile Phe Ile Ser Ser Val
1               5                   10                  15
Gln Lys (2) INFORMATION FOR SEQ ID NO:24:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:24:

Val Phe Gln Val Val Glu Ser Thr Arg Pro Gly Lys
1               5                   10

(2) INFORMATION FOR SEQ ID NO:25:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:25:

Val Trp Leu Gly Glu Thr Ser Ser Ala Tyr Gly Gly Ala
1               5                   10

(2) INFORMATION FOR SEQ ID NO:26:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:26:

Arg Gln Val Phe Phe Gly Ala Gly Asn Tyr His Leu Val Asp Glu Asn
1               5                   10                  15

Phe Asp Pro Leu Pro Asp Tyr Trp Leu Ser Leu Leu Phe Lys Lys Leu
            20                  25                  30

Val Gly Thr Lys Val Leu
        35

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:27:

Tyr Lys Glu Gly Asp Leu Thr Leu Tyr Ala Ile Asn Leu His Asn Val
1               5                   10                  15

Thr Lys (2) INFORMATION FOR SEQ ID NO:28:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:28:

Ser Val Gln Leu Asn Gly Leu Thr Leu Lys
1               5                   10

(2) INFORMATION FOR SEQ ID NO:29:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO -continued (xi) SEQUENCE DESCRIPTION: SEQ ID NO:29:

Pro Leu Arg Pro Gly Ser Ser Leu Gly Leu Pro Ala Phe Ser Tyr Ser
1               5                   10                  15

Phe Phe Val Ile Arg Asn Ala Lys
            20

HUMAN PLATELET HEPARANASE POLYPEPTIDES, POLYNUCLEOTIDE MOLECULES THAT ENCODE THEM, AND METHODS FOR THE IDENTIFICATION OF COMPOUNDS THAT ALTER HEPARANASE ACTIVITY

CROSS-REFERENCE TO RELATED APPLICATIONS

This application claims the benefit of the following provisional applications: U.S. Ser. No. 60/075,706, filed Feb. 24, 1998, and U.S. Ser. No. 60/079,401, filed Mar. 26, 1998, under 35 USC § 119(e)(1).

BACKGROUND OF THE INVENTION

1. Field of the Invention

The present invention provides isolated human heparanase polypeptides, and the isolated polynucleotide molecules that encode them, as well as vectors and host cells comprising such polynucleotide molecules. The invention also provides a method for the identification of an agent that alters heparanase activity.

2. Related Art

Heparanase is a human enzyme that can degrade both heparin proteoglycans (HPG) and heparan sulfate proteoglycans (HSPG). Heparanase activity in mammalian cells is well known. The activity has been identified in various melanoma cells (Nakajima, et al., Cancer Letters 31: 277–283, 1986), mammary adenocarcinoma cells (Parish, et al., Int. J. Cancer, 40: 511–518, 1987), leukemic cells (Yahalom, et al., Leukemia Research 12: 711–717, 1988), prostate carcinoma cells (Kosir, et al., J. Surg. Res. 67: 98–105, 1997), mast cells (Ogren and Lindahl, J. Biol. Chem. 250: 2690–2697, 1975), macrophages (Savion, et al., J. Cell. Physiol, 130: 85–92, 1987), mononuclear cells (Sewell, et al., Biochem. J. 264: 777–783, 1989), neutrophils (Matzner, et al. 51: 519–524, 1992, T-cells (Vettel et al., Eur J. Immunol. 21: 2247–2251, 1991), platelets (Haimovitz-Friedman, et al., Blood 78: 789–796, 1991), endothelial cells (Godder, et al., J. Cell Physiol. 148: 274–280, 1991), and placenta (Klein and von Figura, BBRC 73: 569, 1976). An earlier report that human platelet heparanase is a member of the CXC chemokine family (Hoogewerf et al., J.Biol. Chem. 270: 3268–3277) is in error.

Elevated heparanase activity has been documented in mobile, invasive cells. Examples include invasive melanoma, lymphoma, mastocytoma, mammary adenocarcinoma, leukemia, and rheumatoid fibroblasts. Heparanase activity has also been documented in non-pathologic situations involving the migration of lymphocytes, neutrophils, macrophages, eosinophils and platelets (Vlodavsky et al.,Invasion Metastasis 12: 112–127, 1992).

A number of uses have been proposed for bacterial heparanases. One such use is described in Freed et al. (Ann. Biomed. Eng. 21: 67–76 (1993)), wherein purified bacterial heparanase is immobilized onto filters and connected to extracorporeal devices for use in the degradation of heparin and the neutralization of its anticoagulant properties post surgery.

Other proposed uses for bacterial heparanases include the use of heparanase in a method for inhibiting angiogenesis (U.S. Pat. No. 5,567,417), an application of the enzyme as a means of decreasing inflammatory responses (WO 97/11684), and the use of heparanase-inhibiting compositions for preventing tumor metastasis (U.S. Pat. No. 4,882,318).

In view of the observation that heparanase activity is present in mobile, invasive cells associated with pathologic states, it may be hypothesized that an inhibitor of heparanase would broadly influence the invasive potential of these diverse cells. Further, inhibition of heparan sulfate degradation would inhibit the release of bound growth factors and other biologic response modifiers that would, if released, fuel the growth of adjacent tissues and provide a supportive environment for cell growth (Rapraeger et al., Science 252: 1705–1708, 11991). Inhibitors of heparanase activity would also be of value in the treatment of arthritis, asthma, and other inflammatory diseases, vascular restenosis, atherosclerosis, tumor growth and progression, and fibroproliferative disorders.

A major obstacle to designing a screening assay for the identification of inhibitors of mammalian heparanase activity has been the difficulty of purifying any mammalian heparanase to homogeneity so as to determine its structure, including its amino acid sequence. For this reason, therapeutic applications of mammalian heparanase, or of inhibitors of mammalian heparanase, have been based on research carried out using bacterial heparanase.

WO 91/02977 describes a substantially, but partially, purified heparanase produced by cation exchange resin chromatography and the affinity absorbent purification of heparanase-containing extract from the human SK-HEP-1 cell line. WO 91/02977 also describes a method of promoting wound healing utilizing compositions comprising a "purified" form of heparanase. This enzyme was not thoroughly characterized, and its amino acid sequence was not determined. WO 98/03638 describes a method for the pourification of mammalian heparanase from a heparanase-containing material, such as human platelets. However, the amino acid sequence of this heparanase, and the sequence of the polynucleotide molecule that encodes it, are not disclosed in this reference. Furthermore, this heparanase is characterized only as having a native molecular mass of about 50 kDa, and as degrading both heparin and heparan sulfate.

Although a number of assays for heparanase have been described, the complexity of the HSPG substrate has caused methods for assay of heparanase activity to be rudimentary and lacking in kinetic sophistication. Haimovitz-Friedman et al. (Blood 78: 789–796, 1991) describe an assay for heparanase activity that involves the culturing of endothelial cells in radiolabeled $^{35}SO_4$ to produce radiolabeled heparan sulfate proteoglycans, the removal of the cells which leaves the deposited extracellular matrix that contains the $^{35}S$-HSPG, the addition of potential sources of heparanase activity, and the detection of possible activity by passing the supernatant from the radiolabeled extracellular matrix over a gel filtration column and monitoring for changes of the size of the radiolabeled material that would indicate that HSPG degradation had taken place. However, this assay cannot be used in a high-throughput screening format.

Nakajima et al. (Anal. Biochem. 196: 162–171, 1986) describe a solid-phase substrate for the assay of melanoma heparanase activity. Heparan sulfate from bovine lung is chemically radiolabeled by reacting it with $[^{14}C]$-acetic anhydride. Free amino groups of the $[^{14}C]$-heparan sulfate were acetylated and the reducing termini were aminated. The $[^{14}C]$-heparan sulfate was chemically coupled to an agarose support via the introduced amine groups on the reducing termini. However, the usefulness of the Nakajima et al. assay is limited by the fact that the substrate is an extensively chemically modified form of naturally occurring heparan sulfate.

Khan and Newman (*Anal. Biochem.* 196: 373–376, 1991) describe an indirect assay for heparanase activity. In this assay, heparin is quantitated by its ability to interfere with the color development between a protein and the dye Coomassie brilliant blue. Heparanase activity is detected by the loss of this interference. This assay is limited in use for screening because it is so indirect that other non-heparin compounds could also interfere with the protein-dye reaction.

In view of the foregoing, it will be clear that there is a need in the art for recombinantly produced human heparanase.

SUMMARY OF THE INVENTION

The present invention provides isolated nucleic acid molecules comprising a polynucleotide encoding human heparanase polypeptides. Unless otherwise indicated, any reference herein to a "human heparanase polypeptide" will be understood to encompass human pre-pro-heparanase, pro-heparanase, and both the 8 kDa and the 56 kDa subunits of the human heparanase enzyme. Pre-pro-heparanase refers to an amino acid sequence which includes a leader sequence, and which can be processed to remove 48 amino acids yielding both the 8 kDa and the 56 kDa subunits of the human heparanase enzyme; pro-heparanase refers to the enzymatically inactive, full-length molecule from which the signal peptide has been removed and which can be processed to yield both the 8 kDa and the 56 kDa subunits of the human heparanase enzyme. Fragments of human heparanase polypeptides are also provided. Unless otherwise indicated, any reference herein to a "human heparanase enzyme" will be understood to refer to a non-covalently associated complex of the 56 kDa and the 8 kDa human heparanase polypeptides.

In a preferred embodiment, the nucleic acid molecules comprise an isolated polynucleotide having a nucleotide sequence encoding a human heparanase polypeptide selected from the group consisting of: a human pre-pro-heparanase polypeptide having the complete amino acid sequence of SEQ ID NO:2; a human pro-heparanase polypeptide having the amino acid sequence at residues 23 through 530 of SEQ ID NO:2; the 8 kDa subunit of human heparanase having the amino acid sequence at residues 23 through 96 of SEQ ID NO:2; and the 56 kDa subunit of human heparanase having the amino acid sequence at residues 145 through 530 of SEQ ID NO:2.

In another preferred embodiment, the nucleic acid molecules comprise a polynucleotide having a nucleotide sequence selected from the group consisting of the complete nucleotide sequence of SEQ ID NO: 1, the nucleotide sequence at residues 67 through 1590 of SEQ ID NO: 1, the nucleotide sequence at residues 433 through 1590 of SEQ ID NO:1, and the nucleotide sequence at residues 67 through 288 of SEQ ID NO:1. In another aspect, the invention provides an isolated nucleic acid molecule comprising a polynucleotide which hybridizes under stringent conditions to a polynucleotide encoding a human heparanase polypeptide, or fragments thereof.

The present invention also provides vectors comprising the isolated nucleic acid molecules of the invention, host cells into which such vectors have been introduced, and recombinant methods of obtaining a human heparanase polypeptide comprising culturing the above-described host cell and isolating the human heparanase polypeptides.

In another aspect, the invention provides isolated human heparanase polypeptides, as well as fragments thereof. In a preferred embodiment, the human heparanase polypeptide comprises an amino acid sequence selected from the group consisting of: an amino acid sequence of a human pre-pro-heparanase having the complete amino acid sequence of SEQ ID NO:2, an amino acid sequence of a human pro-heparanase having the amino acid sequence at residues 23 through 530 of SEQ ID NO:2, an amino acid sequence of the 8 kDa subunit of human heparanase having amino acid sequence at residues 23 through 96 of SEQ ID NO:2, and an amino acid sequence of the 56 kDa subunit of human heparanase having the amino acid sequence at residues 145 through 530 of SEQ ID NO:2.

In a preferred embodiment, the human heparanase polypeptides of the invention are expressed from an isolated nucleic acid molecule encoding a polypeptide selected from the group consisting of a human pre-pro-heparanase polypeptide having the complete amino acid sequence of SEQ ID NO:2; a human pro-heparanase polypeptide having the amino acid sequence at residues 23 through 530 of SEQ ID NO:2; the 8 kDa subunit of human heparanase having the amino acid sequence at residues 23 through 96 of SEQ ID NO:2; and the 56 kDa subunit of human heparanase having the amino acid sequence at residues 145 through 530 of SEQ ID NO:2.

In another preferred embodiment, the human heparanase polypeptides of the invention are expressed from an isolated nucleic acid molecule comprising a polynucleotide having a nucleotide sequence selected from the group consisting of: the complete nucleotide sequence of SEQ ID NO: 1; the nucleotide sequence at residues 67 through 1590 of SEQ ID NO:1; the nucleotide sequence at residues 433 through 1590 of SEQ ID NO:1; and the nucleotide sequence at residues 67 through 288 of SEQ ID NO: 1. Isolated antibodies, both polyclonal and monoclonal, that bind specifically to human heparanase polypeptides are also provided.

The invention also provides a human heparanase enzyme comprising an isolated human heparanase polypeptide comprising the amino acid sequence at residues 145 through 530 of SEQ ID NO:2 and an isolated human heparanase polypeptide comprising the amino acid sequence at residues 23 through 96 of SEQ ID NO:2.

The invention also provides a method for the identification of an agent that alters heparanase activity, said method comprising:

(a) determining the activity of any of the above-described human heparanase enzyme
   (i) in the presence of a test agent; and
   (ii) in the absence of said test agent; and (b) comparing the heparanase activity determined in step (a)(i) to the heparanase activity determined in step (a)(ii); whereby a change in heparanase activity in sample (a)(i) has compared to sample (a)(ii) indicates that said agent alters the activity of said human heparanase.

BRIEF DESCRIPTION OF THE FIGURES

FIG. 2A is a graph depicting the results of size-exclusion chromatography of a sample from pooled fractions 36–66 on Superdex-75. The buffer used was 10 mM sodium acetate, pH 5.0, 10 mM βOG, 1 mM DTT, and 0.50 M NaCl. Heparanase activity elutes at a position corresponding to MW~40–60,000 (shaded area). FIG. 2B is an SDS-PAGE analysis of pools 1–7, showing a strong band at MW=40,000 in the active fraction (lane 4). The 56 kDa heparanase is just faintly visible in this fraction. Note that the low MW peptides associated with chemokines are prominent in lane 7.

FIGS. 7A, 7B, and 7C show the amino acid (SEQ ID NO: 2) and nucleotide sequence (SEQ ID NO: 1) of human heparanase polypeptides. Arrows denote sites of processing at: Ala22-Gln23 (to remove signal peptide from pre-pro-heparanase); Glu96-Ser97 (to give the 74 residue 8 kDa polypeptide) and Gln144-Lys145 (to give the C-terminal 56 kDa polypeptide). Start and stop codons are underlined.

FIG. 8 shows the sequence of 16 peptide fragments (SEQ ID NOS: 14–29) of pre-proheparanase, which was determined directly as described in Example 3.

DETAILED DESCRIPTION

Figure 1:
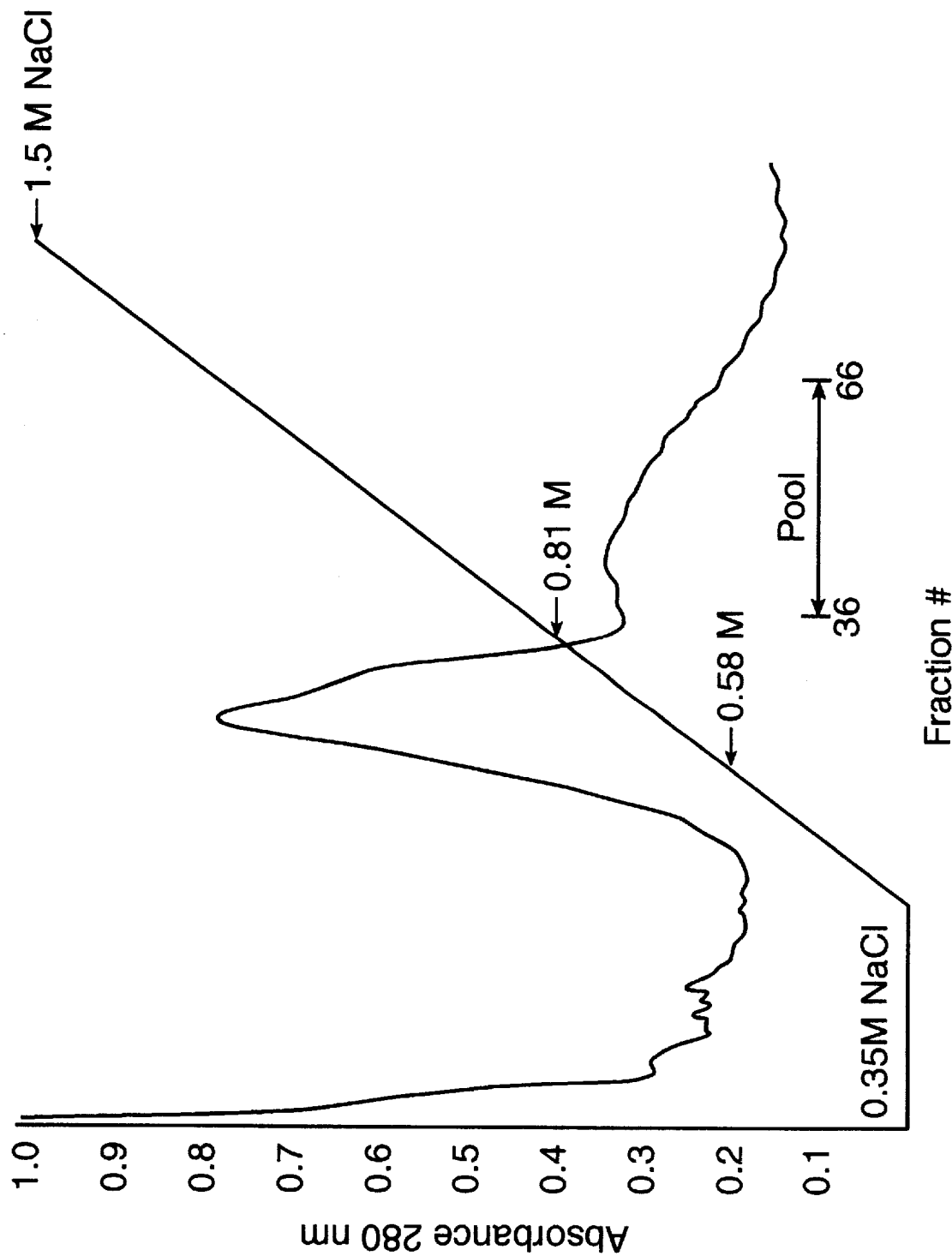
FIG. 1 is a graph depicting the results of chromatography of crude human platelet lysate on a column of Heparin Sepharose CL6B, using a buffer of 10 mM sodium acetate, pH 5.0, 10 mM βOG, 1 mM DTT, and 0.35 M NaCl. For the gradient, the same buffer was used with up to 1.5 M NaCl. Heparanase activity elutes in a broad region defined by fractions 36–66.

The present invention provides the first isolation of a cDNA encoding a mammalian heparanase. The human heparanase of the invention is produced by the processing of a glycoprotein precursor, designated herein as pre-pro-heparanase, having a signal sequence and six consensus sequences for N-linked glycosylation. The full length protein contains 530 amino acids, including an N-terminal signal sequence of 22 residues; the sequence of the full length protein is given in SEQ ID NO: 2. Removal of the signal peptide yields an N-terminal glutamine residue which cyclizes to pyrrolidonecarboxylic acid (PCA), thus blocking the protein for Edman degradation. The resulting 508 residue protein, also referred to herein as pro-heparanase, or the 65 kDa polypeptide, has an amino acid sequence corresponding to amino acid residues 23 to 530 of SEQ ID NO: 2. Pro-heparanase is not catalytically active until it is processed further by cleavage of the $Glu_{96}$-$Ser_{97}$ and $Gln_{144}$-$Lys_{145}$ bonds. These cleavages yield two polypeptides of 74 and 386 amino acids, which comprise the 8 and 56 kDa chains of human heparanase, respectively. The 8 kDa polypeptide has the amino acid sequence corresponding to amino acid residues 23 to 96 of SEQ ID NO: 2, while the 56 kDa polypeptide has the amino acid sequence corresponding to amino acid residues 145 to 530 of SEQ ID NO: 2 In this process, 48 amino acids (residues 97–144 of SEQ ID NO: 2) are excised. The active heparanase consists of non-covalently associated 56 kDa and 8 kDa polypeptides.

Of course, due to the degeneracy of the genetic code, two DNA sequences may differ and yet encode identical amino acid sequences. The present invention thus provides isolated nucleic acid molecules having a polynucleotide sequence encoding any of the human heparanase polypeptides of the invention. Thus, the present invention provides isolated nucleic acid molecules comprising a nucleotide sequence encoding the human pre-pro-heparanase polypeptide, which includes the leader sequence, said polypeptide having the complete amino acid sequence given in SEQ ID NO:2. The invention also provides isolated nucleic acid molecules comprising a nucleotide sequence encoding the human pro-heparanase polypeptide without the leader sequence, said polypeptide having the amino acid sequence at positions 23–530 of SEQ ID NO:2. The invention also provides isolated nucleic acid molecules comprising a nucleotide sequence encoding the 8 kDa subunit of the human heparanase polypeptide, said polypeptide having the amino acid sequence at positions 23–96 of SEQ ID NO:2. The invention also provides isolated nucleic acid molecules comprising a nucleotide sequence encoding the 56 kDa subunit of the human heparanase polypeptide, said polypeptide having the amino acid sequence at positions 145–530 of SEQ ID NO:2. Isolated nucleic acid molecules comprising a nucleotide sequence encoding fragments of any of the above-mentioned polypeptides are also included herein.

As used herein, an "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

In a preferred embodiment, the isolated nucleic acid molecule of the invention comprises a polynucleotide having the complete nucleotide sequence given in SEQ ID NO: 1, which corresponds to the nucleotide sequence encoding human pre-pro-heparanase, including the leader sequence, from human platelets. (The first nucleotide of SEQ ID NO: 1 (adenylate-1) aligns with the N-terminal Met-1 residue of SEQ ID NO:2.) In another preferred embodiment, the isolated nucleic acid molecule of the invention comprises a polynucleotide having the nucleotide sequence of residues 67–1590 of SEQ ID NO: 1, which corresponds to the nucleotide sequence encoding human platelet pro-heparanase without the leader sequences. In another preferred embodiment, the isolated nucleic acid molecule of the invention comprises a polynucleotide having the nucleotide sequence of nucleotide residues 67–288 of SEQ ID NO: 1, or nucleotide residues 433–1590 of SEQ ID NO: 1, which correspond to the nucleotide sequence encoding the 8 kDa subunit and the 56 kDa subunit of the human heparanase enzyme, respectively.

As is described in Example 4, both manual and automated sequencing methods were used to obtain or verify the nucleotide sequence of human heparanase. The human heparanase nucleotide sequences of the present invention were obtained for both DNA strands, and are believed to be 100% accurate. However, as is known in the art, nucleotide sequence obtained by such automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation. However, the likelihood that the sequence contains a frameshift is minimal in this instance, because the amino acid sequence of a large part of human heparanase, determined by direct sequencing of human heparanase peptides, corresponds to the amino acid sequence deduced from the nucleotide sequence of the polynucleotide molecule encoding human heparanase.

The human heparanase DNA of the present invention includes cDNA, chemically synthesized DNA, DNA isolated by PCR, genomic DNA, and combinations thereof. One of ordinary skill would readily be able to obtain isolated genomic human heparanase DNA by screening a genomic library with the human heparanase cDNA described herein, using methods that are well known in the art. RNA transcribed from human heparanase DNA is also encompassed by the present invention.

In another aspect, the invention provides an isolated nucleic acid molecule comprising a polynucleotide which hybridizes under stringent conditions to a portion of the nucleic acid molecules described above, e.g., to about 15 nucleotides, preferably to at least about 20 nucleotides, more preferably to at least about 30 nucleotides, and still more preferably from about 30 to at least about 100 nucleotides, of one of the previously described nucleic acid molecules. Such portions of nucleic acid molecules having the described lengths refer to, e.g., at least about 15 contiguous nucleotides of the reference nucleic acid molecule. By stringent hybridization conditions is intended overnight incubation at about 42° C. for about 2.5 hours in 6×SSC/ 0.1% SDS, followed by washing of the filters in 1.0×SSC at 65° C., 0.1% SDS.

Fragments of the human heparanase-encoding nucleic acid molecules described herein, as well as polynucleotides capable of hybridizing to such nucleic acid molecules may be used as a probe or as primers in a polymerase chain reaction (PCR). Such probes may be used, e.g., to detect the presence of human heparanase nucleic acids in in vitro assays, as well as in Southern and northern blots. Cell types expressing human heparanase may also be identified by the use of such probes. Procedures for Southern blots, northern blots, and PCR are well known in the art. Consequently, the skilled artisan will be able to design suitable probes and primers comprising fragments of the human heparanase nucleic acid molecules of the invention for use in the desired procedure, and to perform these procedures, without undue experimentation.

As this is the first time that a cDNA from a mammalian heparanase has been isolated and characterized, the above-described techniques also allow fragments of the human heparanase-encoding nucleic acid molecules of the invention to be used to detect the presence of, and to isolate, heparanase nucleic acids in a variety of mammalian species. For example, knowledge of the primary structure of this cDNA has enabled identification of mouse platelet heparanase and a heparanase homolog in human prostate carcinoma.

Also provided herein are isolated human heparanase polypeptides having the amino acid sequence given in SEQ ID NO:2, or a polypeptide comprising a fragment thereof. Thus, in one embodiment, the invention provides an isolated polypeptide having the complete amino acid sequence given in SEQ ID NO:2, which encodes pre-proheparanase, and which includes a leader sequence of about 22 amino acids, corresponding to amino acids 1 through 530 of SEQ ID NO:2. In another embodiment, the invention provides an isolated polypeptide having the amino acid sequence corresponding to amino acid residues 23 through 530 of SEQ ID NO:2, which encodes proheparanase. In another embodiment, the invention provides an isolated polypeptide having the amino acid sequence corresponding to amino acid residues 23 through 96 of SEQ ID NO:2, which encodes the 8 kDa subunit of human heparanase. In yet another embodiment, the invention provides an isolated polypeptide having the amino acid sequence corresponding to amino acid residues 145 through 530 of SEQ ID NO:2, which corresponds to the 56 kDa subunit of human heparanase.

In another aspect, the invention provides human heparanase polypeptides with or without associated native pattern glycosylation. Human heparanase expressed in yeast or mammalian expression systems (discussed below) may be similar to or significantly different from a native human heparanase polypeptide in molecular weight and glycosylation pattern. Of course, expression of human heparanase in bacterial expression systems will provide non-glycosylated human heparanase.

The polypeptides of the present invention are preferably provided in an isolated form, are preferably substantially purified, and most preferably are purified to homogeneity. Human heparanase polypeptides may be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography.

In a preferred embodiment, heparanase is purified to homogeneity from human platelet extracts by size exclusion and affinity chromatography on immobilized heparin (see Example 1). The heparanase so produced has an activity of about 1000 units heparanase activity per $\mu$g heparanase protein (units/$\mu$g) to about 12,000 units/$\mu$g, preferably between about 3000 units/$\mu$g to about 10,000 units/$\mu$g, and more preferably, between about 4000 units/$\mu$g to about 8000 units/$\mu$g, where one unit of enzyme activity is defined as the amount of enzyme which, under standard assay conditions, leads to the breakdown of 1% of heparan $^{35}SO_4$ radioactivity per hour. Breakdown of heparan $^{35}SO_4$ radioactivity is measured by the amount of radiolabel that passes through a 30,000 MW cut-off membrane. Accordingly, 1 unit=1% cpm, which is greater than or equal to 30,000 MW/hour using the assay described in Example 2.

The invention also provides variants of human heparanase polypeptides, or the polynucleotide molecules encoding them, such as those that may be obtained by mutation of native human heparanase-encoding nucleotide sequences, for example. A human heparanase variant, as referred to herein, is a polypeptide substantially identical to a native human heparanase polypeptide but which has an amino acid sequence different from that of native human heparanase polypeptide because of one or more deletions, insertions, or substitutions in the amino acid sequence. The variant amino acid or nucleotide sequence is preferably at least about 80% identical, more preferably at least about 90% identical, and most preferably at least about 95% identical, to a sequence of a native human heparanase polypeptide. Thus, a variant nucleotide sequence which contains, for example, 5 point mutations for every one hundred nucleotides, as compared to a native human heparanase gene, will be 95% identical to the native protein. The percentage of sequence between a native and a variant human heparanase sequence may also be determined, for example, by comparing the two sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman (*Adv. Appl. Math.* 2: 482–489 (1981)).

Alterations of the native amino acid sequence may be accomplished by any of a number of known techniques. For example, mutations may be introduced into the polynucleotide encoding a polypeptide at particular locations by procedures well known to the skilled artisan, such as oligonucleotide-directed mutagenesis, which is described by Walder et al. (*Gene* 42:133 (1986)); Bauer et al. (*Gene* 37:73 (1985)); Craik (*BioTechniques*, January 1985, pp. 12–19); Smith et al. (*Genetic Engineering: Principles and Methods*, Plenum Press (1981)); and U.S. Pat. Nos. 4,518,584 and 4,737,462.

Human heparanase variants within the scope of the invention may comprise conservatively substituted sequences, meaning that one or more amino acid residues of a human heparanase polypeptide are replaced by different residues that do not alter the secondary and/or tertiary structure of the human heparanase polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges may be found in Bowie et al., *Science* 247:1306–1310 (1990). Other human heparanase variants which might retain substantially the biological activities of human heparanase are those where amino acid substitutions have been made in areas outside functional regions of the protein.

The present invention also relates to vectors comprising the polynucleotide molecules of the invention, as well as host cells transformed with such vectors. Any of the polynucleotide molecules of the invention may be joined to a vector, which generally includes a selectable marker and an origin of replication, for propagation in a host. Because the invention also provides human heparanase polypeptides expressed from the polynucleotide molecules described above, vectors for the expression of human heparanase are preferred. The vectors include DNA encoding any of the human heparanase polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding human heparanase. Thus, a promoter nucleotide sequence is operably linked to a human heparanase DNA sequence if the promoter nucleotide sequence directs the transcription of the human heparanase sequence.

Selection of suitable vectors to be used for the cloning of polynucleotide molecules encoding human heparanase, or for the expression of human heparanase polypeptides, will of course depend upon the host cell in which the vector will be transformed, and, where applicable, the host cell from which the human heparanase polypeptide is to be expressed. Suitable host cells for expression of human heparanase polypeptides include prokaryotes, yeast, and higher eukaryotic cells, each of which is discussed below.

The human heparanase polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the human heparanase sequence so that human heparanase is translated as a fusion protein comprising the signal peptide. A signal peptide that is functional in the intended host cell promotes extracellular secretion of the human heparanase polypeptide. Preferably, the signal sequence will be cleaved from the human pre-pro heparanase polypeptide upon secretion of human heparanase from the cell. Non-limiting examples of signal sequences that can be used in practicing the invention include the yeast I-factor and the honeybee melatin leader in sf9 insect cells.

In one embodiment, the human heparanase polypeptide comprises a fusion protein which includes a heterologous region used to facilitate purification of the polypeptide. Many of the available peptides used for such a function allow selective binding of the fusion protein to a binding partner. For example, the human heparanase polypeptide may be modified to comprise a peptide to form a fusion protein which specifically binds to a binding partner, or peptide tag. Non-limiting examples of such peptide tags include the 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

Suitable host cells for expression of human heparanase polypeptides include prokaryotes, yeast, and higher eukaryotic cells. Suitable prokaryotic hosts to be used for the expression of human heparanase include bacteria of the genera Escherichia, Bacillus, and Salmonella, as well as members of the genera Pseudomonas, Streptomyces, and Staphylococcus.

The isolated nucleic acid molecules of the invention are preferably cloned into a vector designed for expression in eukaryotic cells, rather than into a vector designed for expression in prokaryotic cells. Eukaryotic cells are preferred for expression of genes obtained from higher eukaryotes because the signals for synthesis, processing, and secretion of these proteins are usually recognized, whereas this is often not true for prokaryotic hosts (Ausubel, et al., ed., in Short Protocols in Molecular Biology, 2nd edition, John Wiley & Sons, publishers, pg. 16–49, 1992.). In the case of the human platelet heparanase, there are 6 consensus sequences for N-linked glycosylation, and other sites of post-translational modification can be predicted for Ser/Thr/Tyr phosphorylation and O-glycosylation. Eukaryotic hosts may include, but are not limited to, the following: insect cells, African green monkey kidney cells (COS cells), Chinese hamster ovary cells (CHO cells), human 293 cells, and murine 3T3 fibroblasts.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

Human heparanase may also be expressed in yeast host cells from genera including Saccharomyces, Pichia, and Kluveromyces. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of human heparanase polypeptides expressed in yeast hosts may be accomplished by the inclusion of nucleotide sequence encoding the yeast factor leader sequence at the 5' end of the human heparanase-encoding nucleotide sequence.

Insect host cell culture systems may also be used for the expression of human heparanase polypeptides. In a preferred embodiment, the human heparanase polypeptides of the invention are expressed using a baculovirus expression system. Further information regarding the use of baculovirus systems for the expression of heterologous proteins in insect cells are reviewed by Luckow and Summers, *Bio/Technology* 6:47 (1988).

In another preferred embodiment, the human heparanase polypeptide is expressed in mammalian host cells. Non-limiting examples of suitable mammalian cell lines include the COS-7 line of monkey kidney cells (Gluzman et al., *Cell* 23:175 (1981)), Chinese hamster ovary (CHO) cells, and human 293 cells.

The choice of a suitable expression vector for expression of the human heparanase polypeptides of the invention will of course depend upon the specific host cell to be used, and is within the skill of the ordinary artisan. Examples of suitable expression vectors include pcDNA3 (Invitrogen) and pSVL (Pharmacia Biotech). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

Also provided herein are isolated human heparanase polypeptides having the amino acid sequence given in SEQ ID NO:2, or a polypeptide comprising a fragment thereof. Such isolated human heparanase polypeptides are preferably substantially purified, using a procedure such as the one detailed below in Example 2.

The present invention also provides a method of screening for agents that alter heparanase activity. In one aspect, the invention provides a method for the identification of an agent that decreases or inhibits heparanase activity. In another aspect, the invention provides a method for the identification of an agent that enhances or increases heparanase activity.

An agent that enhances or increases heparanase activity may be used, for example, for wound healing or as a means for the blocking of angiogenesis or inflammation. Applications for an agent that decreases or inhibits heparanase activity are described below.

Elevated heparanase activity has been documented in mobile, invasive cells. Examples include invasive melanoma, lymphoma, mastocytoma, mammary adenocarcinoma, leukemia, and rheumatoid fibroblasts. This activity has also been documented in non-pathologic situations involving the migration of lymphocytes, neutrophils, macrophages, eosinophils and platelets (Vlodavsky, et al., *Invasion Metastasis* 12:112–127, 1992). An inhibitor of heparanase would therefore broadly influence the invasive potential of these diverse cells.

Inhibition of heparan sulfate degradation will also inhibit the release of bound growth factors and other biologic response modifiers that would, if released, fuel the growth of adjacent tissues, and provide a supportive environment for cell growth (Rapraeger, et al., *Science* 252: 1705–1708, 1991). Inhibitors of heparanase activity would be of value in the treatment of arthritis, asthma, and other inflammatory diseases, vascular restenosis, atherosclerosis, tumor growth and progression, and fibro-proliferative disorders.

Because heparanase breaks down the extracellular matrix with attendant release of growth factors, enzymes, and chemotactic proteins, an agent that inhibits heparanase activity should find therapeutic application in cancer, CNS and neurodegenerative diseases, inflammation, and in cardiovascular diseases such as restenosis following angioplasty and atherosclerosis. The human heparanases of the present invention, both purified and recombinantly produced, may be used for the same applications that have previously been for other heparanases. These applications include, but are not limited to, the acceleration of wound healing, the blocking of angiogenesis, and the degradation of heparin and the neutralization of heparin's anticoagulant properties during surgery, wherein an immobilized heparanase filter is connected to extracorporeal devices to degrade heparin and neutralize its anticoagulant properties during surgery. Immobilization onto filters can be achieved by methods well known in the art, such as those disclosed by Langer et al. (*Biomaterials:Inter-facial Phenomenon and Applications*, Cooper et al, eds., pp. 493–509 (1982)), and in U.S. Pat. Nos. 4,373,023, 4,863,611 and 5,211,850.

Until now, the obstacles to designing a screening assay to find inhibitors of a heparanase that functions in human disease have been the unavailability of detailed molecular information concerning these enzymes and the lack of information about the amino acid sequence of any mammalian heparanase. Mammalian heparanases are low abundance proteins and have proven difficult to purify in quantities sufficient for chemical characterization. Without access to the amino acid sequence, it has not been possible to produce recombinant mammalian heparanase to be used in high-throughput screening efforts or for applications of the enzyme as a tool or therapeutic in its own right where large quantities of the heparanase would be required. Therefore, all prior descriptions of such uses have utilized bacterial heparanases, which have been well-characterized chemically.

The present invention overcomes these problems both by providing methods for purifying to homogeneity the heparanase of human platelets (see Example 2), and by providing the polynucleotide sequence of the gene encoding human heparanase, as well as the deduced amino acid sequence encoded thereby, and thereby providing the necessary tools for recombinant expression of a mammalian heparanase for large-scale production.

Thus, in one embodiment, the invention provides a method for the identification of an agent that alters heparanase activity, said method comprising:

(a) determining the activity of an isolated human heparanase enzyme in the presence of a test agent and in the absence of said test agent, wherein said isolated human heparanase enzyme is selected from the group consisting of
  (i) an isolated human heparanase enzyme comprising
    (a) an isolated human heparanase polypeptide comprising the amino acid sequence at residues 145 through 530 of SEQ ID NO:2, and (b) an isolated human heparanase polypeptide comprising the amino acid sequence at residues 23 through 96 of SEQ ID NO:2;
  (ii) an isolated human heparanase enzyme comprising
    (a) an isolated human heparanase polypeptide expressed from an isolated nucleic acid molecule comprising a polynucleotide having the nucleotide sequence at residues 433 through 1590 of SEQ ID NO:1, and (b) an isolated human heparanase polypeptide expressed from an isolated nucleic acid molecule comprising a polynucleotide having the nucleotide sequence at residues 67 through 288 of SEQ ID NO: 1; and
  (iii) an isolated human heparanase enzyme comprising
    (a) an isolated human heparanase polypeptide expressed from an isolated nucleic acid molecule comprising a polynucleotide having a sequence at least 95% identical to a polynucleotide having the nucleotide sequence at residues 433 through 1590 of SEQ ID NO: 1, and (b) an isolated human heparanase polypeptide of 15(a) is expressed from an isolated nucleic acid molecule comprising a polynucleotide having a sequence at least 95% identical to a polynucleotide having the nucleotide sequence at residues 67 through 288 of SEQ ID NO:1; and (b) comparing the heparanase activity in the presence of said test agent determined in step (a) to the presence of said test agent determined in the absence of said test agent in step (a);

whereby a change in heparanase activity in the presence of said test agent as compared to the heparanase activity in the presence of said test agent indicates that said agent has altered the activity of said human heparanase enzyme.

Of course, where the heparanase activity of the sample containing the test agent is higher than the activity in the sample lacking the test agent, the agent will have increased heparanase activity. Similarly, where the heparanase activity of the sample containing the test agent is lower than the activity in the sample lacking the test agent, the agent will have inhibited heparanase activity.

Thus, in one preferred embodiment, the above-described method is used for the identification of an agent that increases heparanase activity. In another preferred embodiment, the above-described method is used for the identification of an agent that decreases heparanase activity.

Any known assay for heparanase may be used to determine heparanase activity in step (b). In a preferred embodiment, the assay used for this determination is the assay described in Example 2 and Example 9, below. Other radioactive isotopes may be used in order to generate a radiolabeled substrate. For example, N-acetyl groups in HSPG may be removed by hydrolysis and replaced with tritiated [$^3$H] acetyl moieties (Freeman and Parish, *Biochem J*. 325: 229–237 (1997)). Acetyl groups having a $^{14}$C radiolabel have also been employed (Nakajima et al., *Anal. Biochem*. 196: 162–171 (1986)).

In addition to its application as a target for development of molecules that either enhance (increase) or inhibit (decrease) heparanase activity, the purified heparanase of the subject invention can be used therapeutically for wound healing or as a means of blocking angiogenesis or inflammation. It can also be immobilized onto filters and used to degrade heparin from the blood of patients post-surgery.

Wound treatment can be achieved by administering to an afflicted individual an effective amount of a pharmaceutical composition comprising the purified heparanase, or an agent that enhances heparanase activity, in combination with a pharmaceutically acceptable, preferably slow releasing, carrier. See, e.g., PCT/US90/04772, incorporated herein by reference.

Administration of heparanase for inhibition of angiogenesis can be localized or systemic depending upon the application; doses may vary as well. In treatment of psoriasis or diabetic retinopathy, the heparanase, or an agent capable of enhancing heparanase activity, is delivered in a topical carrier. Biodegradable polymeric implants may be used to deliver the heparanase for treatment of solid tumors. See, e.g., PCT/US 005567417A, incorporated herein by reference.

Heparanase, or an agent that enhances heparanase activity, can also be infused into the vasculature to block accumulation and diapedesis of neutrophils at sites of inflammation with or without added domains to confer selectivity in delivery. See, e.g., WO 9711684, incorporated herein by reference The polypeptides of the present invention may also be used to raise polyclonal and monoclonal antibodies, which are useful in diagnostic assays for detecting human heparanase polypeptide expression. Such antibodies may be prepared by conventional techniques. See, for example, *Antibodies: A Laboratory Manual*, Harlow and Land (eds.), Cold Spring Harbor Laboratory Press, Cold Spring Harbor, N.Y., (1988); *Monoclonal Antibodies, Hybridomas:A New Dimension in Biological Analyses*, Kennet et al. (eds.), Plenum Press, New York (1980).

Having generally described the invention, the same will be more readily understood by reference to the following examples, which are provided by way of illustration and are not intended as limiting.

EXAMPLES

Example 1

Purification of Heparanase from Human Platelets

Platelet-rich plasma ($10^9$ platelets/ml; 1800 ml) was obtained from healthy, informed volunteers by plasmapheresis. The plasma was removed from the platelets by centrifugation (Heldin, et al., *Exp. Cell Res*. 109: 429–437, 1977). Platelets suspended in phosphate buffered saline (PBS; 0.1 original volume) were then stimulated with 1 U/ml thrombin for 5 min at 37° C. This concentration of thrombin has been reported to release 100% of the heparanase activity from platelets (Oldberg, et al., *Biochemistry* 19: 5755–5762, 1980). Alternatively, cells may be lysed directly by hypotonic lysis by exposure of the platelet pellet to water for 10 sec. Following release of enzyme, 100 mM phenylmethylsulfonylfluoride (PMSF) was added to a final concentration of 1 mM, and the suspension was centrifuged at 2000×g for 30 min at 400° C. The supernatant was stored at −80° C. until used for the chromatographic purification of heparanase.

Chromatographic purification of heparanase was performed as follows:

Step I: Heparin-Sepharose Chromatography:

Activated platelet supernatants were pooled and adjusted to contain 1 mM GSH and 1 mM DTT. This pool was loaded (from 0.2 to 2.5 ml/min) onto a column of heparin-Sepharose (1.6×20 cm, 40 ml) equilibrated in 1 mM GSH, 1 mM DTT, 150 mM NaCl, 10 mM NaPO$_4$, pH 7.4. After loading the sample, the column was washed with 200 ml of 0.35 M NaCl, 1 mM DTT, 1 mM GSH, 10 mM sodium acetate, pH 5. The column was then eluted with a 750 ml linear gradient of increasing NaCl concentration from 0.35 M to 1.5 M in the same buffer. Aliquots of each fraction were used for determination of heparanase activity by the assay described below. The elution profile is shown in FIG. 1. Fractions containing heparanase activity (fractions 36–66 in FIG. 1) were pooled and concentrated from about 400 ml to about 10 ml using a stirred cell ultrafiltration module (Amicon) employing a YM-10 membrane (cutoff 10,000 MW). This solution was stored at 4 degrees until further purification. SDS-PAGE analysis of active fractions showed major bands which did not correspond to either the 56,000 (Lys$_{145}$ to Ile$_{530}$ in SEQ ID NO:2) or 65,000 MW (Gln$_{23}$ to Ile$_{530}$ in SEQ ID NO:2) heparanases; these are very minor components which cannot be visualized on gels until they are concentrated and more highly purified.

Figure 2A:
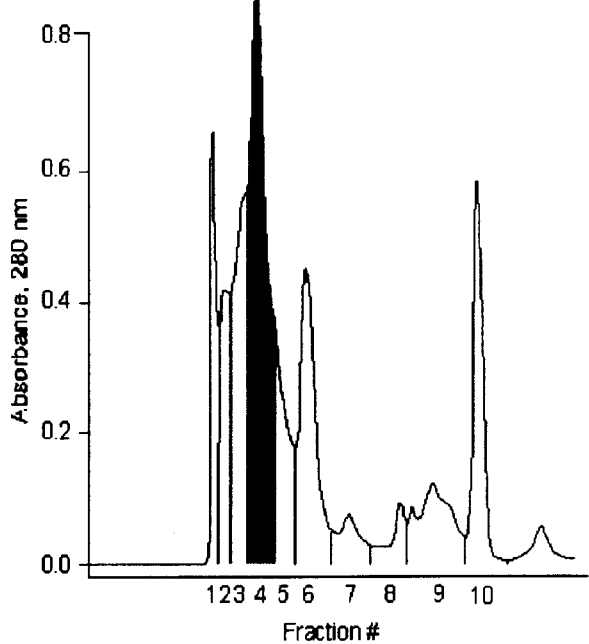
FIGS. 2A and 2B.
Figure 2B:
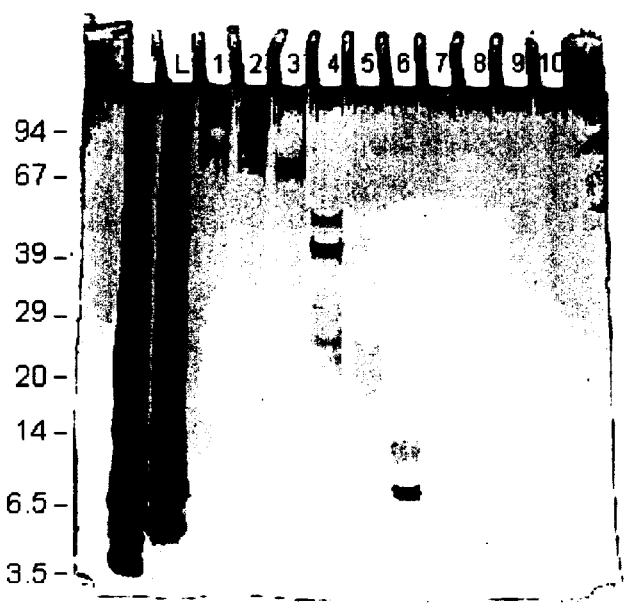

Step II: Size Exclusion Chromatography on Superdex-75:

Concentrated heparanase from Step I was loaded in several 1.0 ml portions on to a column (1.6×60 cm) of Superdex-75 preequilibrated with 10 mM Na acetate. pH 5.0, containing 1 mM DTT, 10 mM J-octylglucoside, and 0.5 M NaCl. The elution profile of FIG. 2 shows that the activity migrates at a position corresponding to a molecular weight of about 50 kDa to about 70 kDa, based upon calibration with known protein standards. SDS-PAGE confirmed the size distribution of fractions over the elution profile. Fractions containing heparanase activity were pooled and stored at 40° C.

Figure 3:
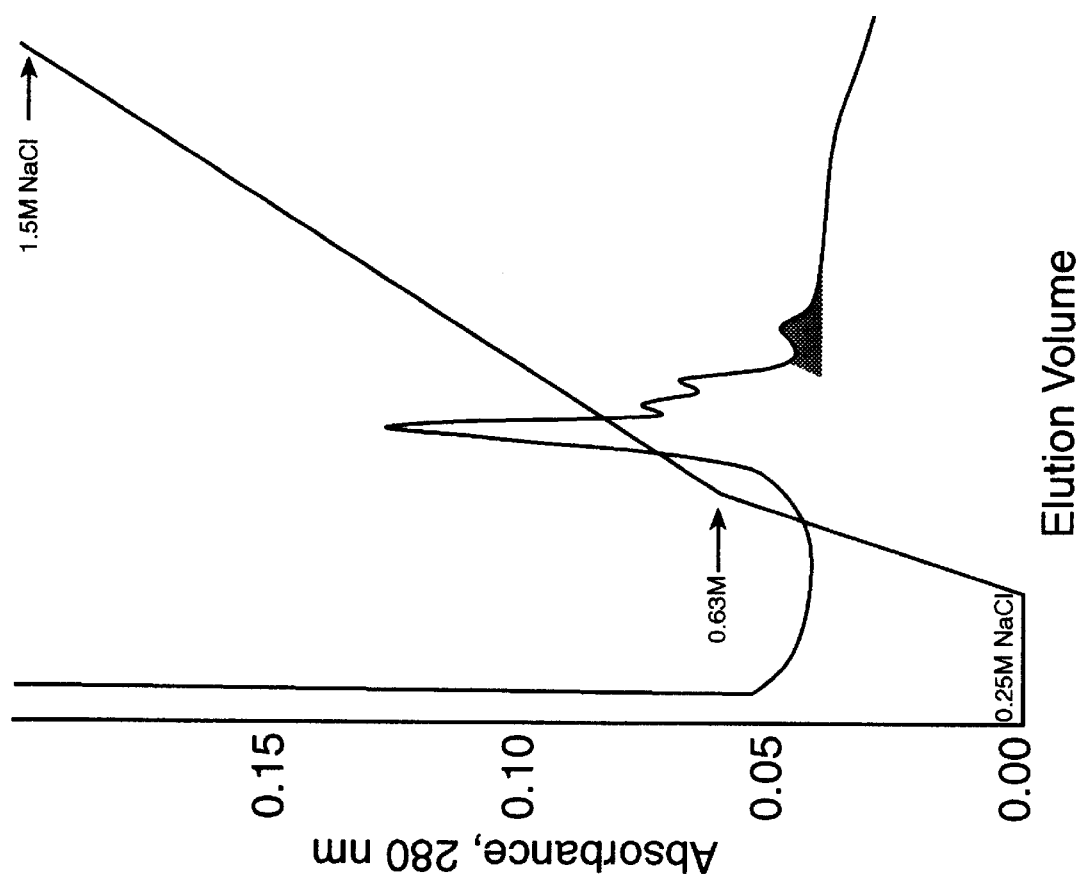
FIG. 3 is a graph depicting the results of chromatography of SEC-Fraction 4 on a Heparin-HiTrap column, pH 7.0. Heparanase activity elutes as the final peak in this separation (shaded area) at a [NaCl]~0.9 M. The 65 kDa heparanase precursor is present in the peak preceding the shaded active peak which contains the 56 kDa+the 8 kDa polypeptides (see FIG. 4). The heparanase peptides can be visualized by silver staining, and the 65 and 56 kDa species may be detected by Western blots using peptide-derived antibodies.
Figure 4:
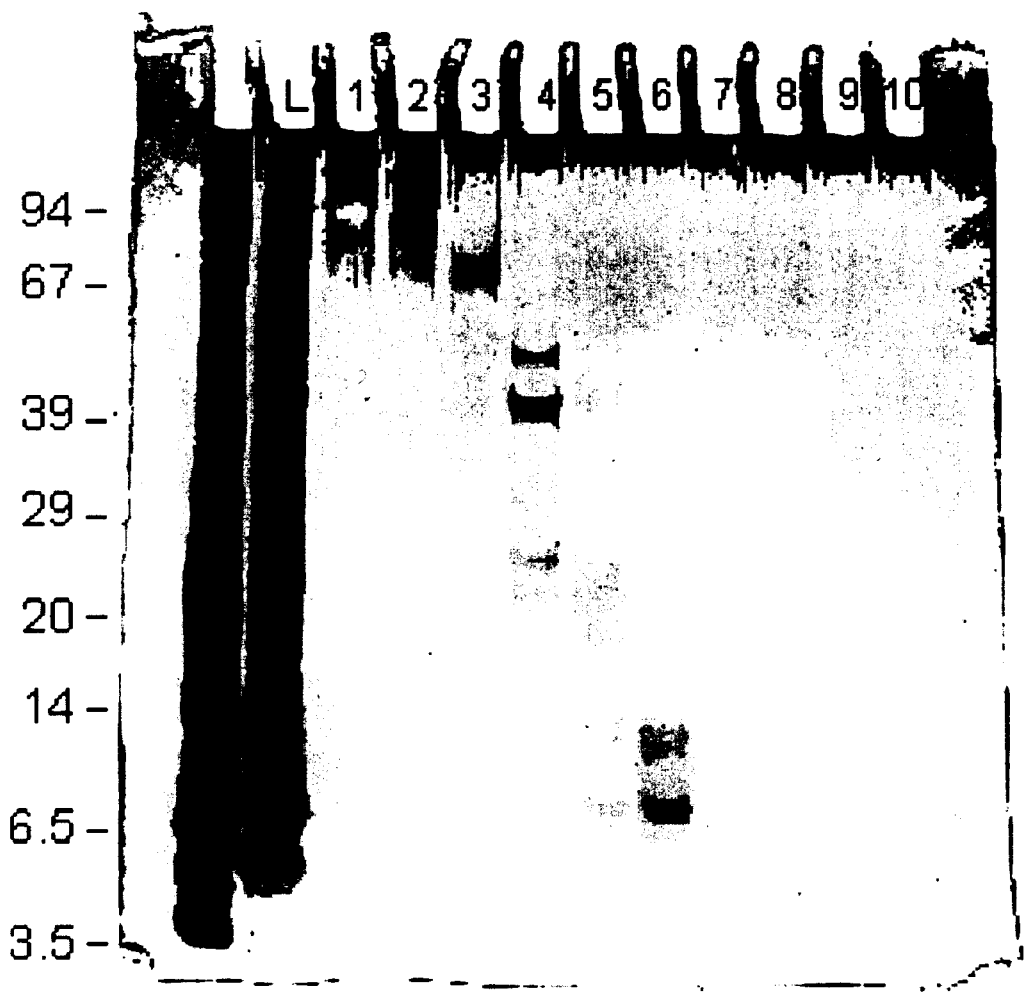
FIG. 4 is an SDS-PAGE gel of purified heparanase. The solution corresponding to the shaded area of FIG. 3 was subjected to non-reducing SDS-PAGE, and two bands are visible by silver staining, one at 56 kDa and one at 8 kDa (corresponding to lane L). Lanes marked 1 and 2 correspond to peaks 1 and 2 of FIG. 5, respectively, that were isolated from the mixture by RP-HPLC.
Figure 5:
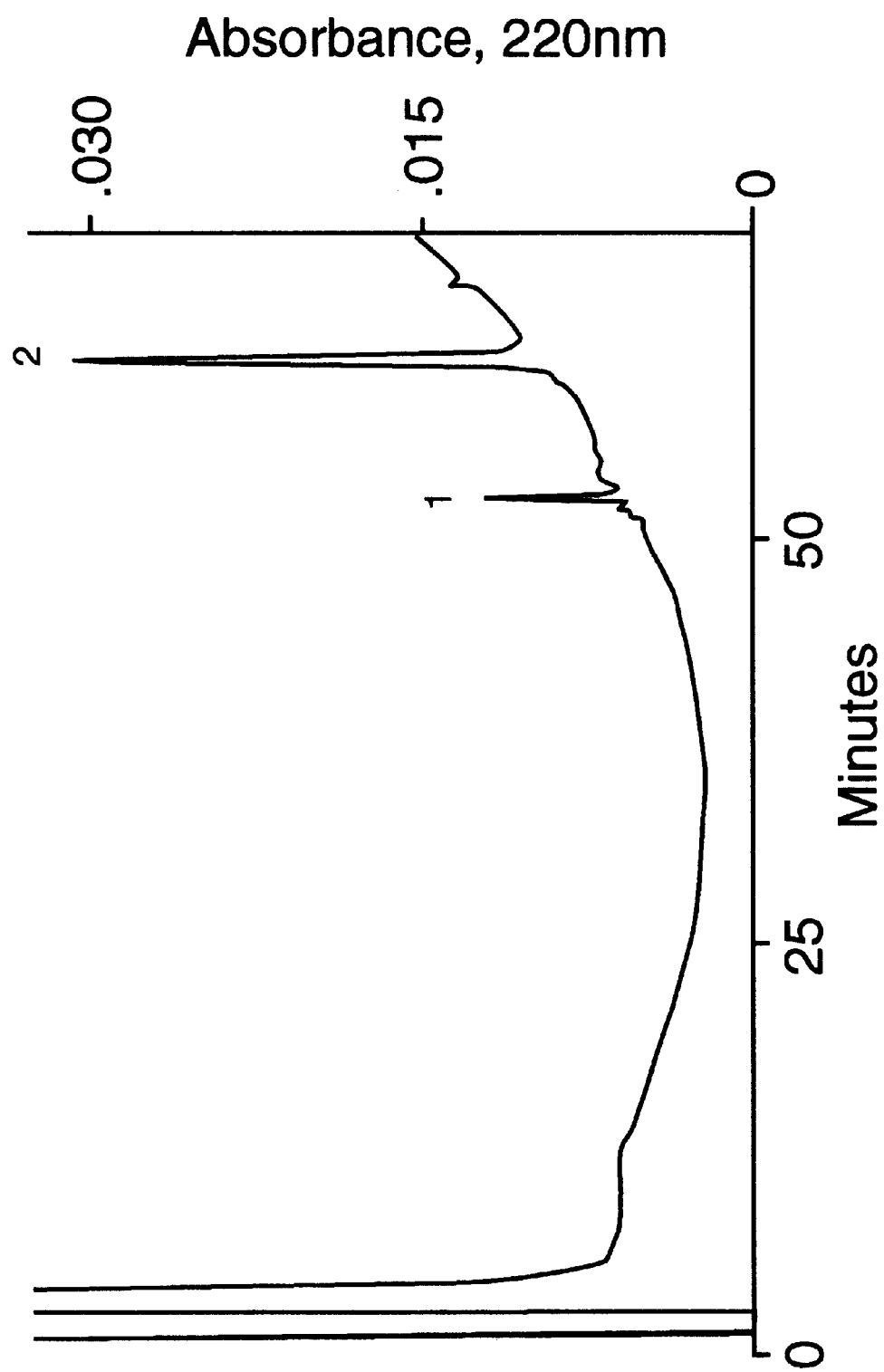
FIG. 5 is a graph depicting the results of reverse-phase HPLC of purified heparanase contained within the shaded area of FIG. 3, and shown to contain both a 56 kDa and an 8 kDa component on SDS-PAGE (see FIG. 4). Separation of the 8 and 56 kDa polypeptides was obtained on a column of Vydac C4 developed in 0.15% TFA with a linear gradient of increasing acetonitrile concentration. Peaks 1 and 2 correspond to the 8 and 56 kDa species, respectively, as shown by SDS-PAGE at lanes 1 and 2 of FIG. 4.

Step III: Heparin HiTrap Column Chromatography:

Pooled heparanase fractions from Step II were diluted 2-fold to reduce the concentration of NaCl to 0.25 M, and this solution was applied to a 1.0 ml Heparin-HiTrap column equilibrated in 10 mM sodium phosphate, pH 7.0, containing 1 mM DTT, 10 mM J-octylglucoside and 0.25 M NaCl. Protein was eluted at a flow rate of 1.0 ml/min with a biphasic gradient of increasing NaCl concentration: 1. 0.25 M to 0.7 M in 10 ml; 0.7 M to 1.5 M in 45 ml. Activity was recovered at a NaCl concentration of near 0.9 M and emerged as a single final peak in the elution profile, indicated by the shaded area in FIG. 3. SDS-PAGE analysis of this peak, run according to the method of Laemmli (*Nature* 227: 680–685, 1970) shows two silver-stained bands migrating at positions corresponding to MW=56,000 and MW=8, 000 (FIG. 4, lane L). Reversed-phase HPLC of the Heparin-HiTrap purified material on a column (1.0×150 mm) of Vydac C4 in 0.15% TFA developed with a linear gradient of increasing acetonitrile concentration (FIG. 5) indicated a major peak at 62 min (peak 2) and a smaller peak at 53 min (peak 1). Analysis of these peaks by SDS-PAGE showed that the 56 kDa protein was in peak 2 (FIG. 4, lane 2) while the 8 kDa polypeptide was in peak 1 (FIG. 4, lane 1). The 8 and 56 kDa species are derived from the same single heparanase precursor; the 8 kDa peptide corresponds to amino acid residues 23 to 96 of SEQ ID NO: 2, and the 56 kDa protein corresponds to amino acid residues 145 to 530 of SEQ ID NO: 2. Gel filtration of the 56 kDa/8 kDa complex in non-denaturing solvents failed to resolve the polypeptides, indicating a strong, non-covalent association. Since both the 8 and 56 kDa polypeptides are closely associated in the final purified protein, it appears that both may be essential for catalytic activity. Separation of the two chains requires a denaturing solvent such as SDS or TFA/acetonitrile.

Characterization of the purified heparanase:

The final yield of heparanase protein from 4000 ml platelet-rich plasma was 20 μg. The preparation was judged to be homogeneous because the two components resolved by SDS-PAGE and HPLC from the material purified by HiTrap chromatography (FIGS. 3, 4, and 5) were shown to be derived by processing of a single 65 kDa proheparanase precursor.

The pH optimum of the purified heparanase was determined by conducting the assay described in Example 2 (the Conventional Assay) in the pH range of 3.5 to 8.0, using a citrate buffer (pH 3.5–6.0), citrate-phosphate buffer (pH 6.5–7.0), and phosphate buffer (pH 7.5–8). Heparanase was active between pH 5.0 and 8.0, with the optimum pH at 5.8.

Enzyme kinetics were not determined for human heparanase, as the heparanase assay described below does not support kinetic analysis (the assay is based upon a single time point reading at 16 hours of hydrolysis of substrate). Examination of the time course of hydrolysis has given variable results ranging from linear to hyperbolic.

Example 2

Assay for Heparanase Activity Using the Conventional Assay

Preparation of $^{35}$S-HSPG (>70 K) for Use in the Heparanase Assay:

$^{35}$S-HSPG (>70 K) was prepared from mice bearing a basement membrane tumor that overproduces HSPG (EHS tumor), using modifications of the method of Ledbetter et al. (*Biochemistry* 26: 988–995 (1987)). Briefly, the radiolabeled HSPG was prepared by injecting C57BL mice bearing the EHS tumor with sodium [$^{35}$S] sulfate (0.5 mCi/mouse) 18 h before harvesting the tumor. The HSPG was extracted from the weighed tumor with 6 volumes (w/v) of Buffer A (3.4 M NaCl, 0.1 M 6-aminohexanoic acid, 0.04 M EDTA, 0.008 M N-ethylmaleimide, 0.002 M PMSF, and 0.05 M Tris-HCl, pH 6.8), by homogenization with a Polytron for 30 s, followed by stirring at 40(for 1 h. Insoluble material was collected by centrifugation (12,000×g for 10 min), and the supernatant was discarded. The insoluble residue was reextracted with 2 volumes (original tumor weight) of Buffer A for 30 min with stirring at 40° C. Insoluble material was again collected by centrifugation, and the supernatant fraction was discarded. The insoluble material was then suspended in 6 volumes of Buffer B (6 M urea, 0.1 M 6-aminohexanoic acid, 0.04 M EDTA, 0.002 M PMSF, and 0.05 M Tris-HCl, pH 6.8), homogenized with an electric homogenizer (Polytron) for 30 s, and stirred for 2 h at 40°

C. The mixture was centrifuged to remove insoluble material, and the supernatant was retained. The insoluble material was reextracted with 2 volumes of Buffer B. The mixture was centrifuged, and the supernatant was combined with the previous supernatant.

$^{35}$S-HSPG was isolated from the Buffer B supernatant by sequential chromatography on anion exchange and gel filtration columns. The Buffer B supernatant was dialyzed overnight against 10 volumes of 6 M urea, 0.15 M NaCl, 0.05 M Tris-HCl, pH 6.8, and was adjusted to contain 0.5% non-ionic detergent (Triton X-100). This supernatant (from 11 g tumor) was chromatographed on a 30 ml column of anion exchange resin (DEAE-Sephacel) equilibrated with 6 M urea, 0.15 M NaCl, 0.05% Triton X-100, 0.05 M Tris-HCl, pH 6.8. After loading the supernatant and washing with the equilibration buffer, the column was developed with a 250 ml linear gradient between 0.15 M NaCl and 1.15 M NaCl (flow=2.0 ml/min). Fractions were sampled for radioactivity, and those containing the $^{35}SO_4$ label that eluted from the DEAE-Sephacel between 0.4 M and 0.8 M NaCl were pooled. The proteoglycan was precipitated by the addition of 4 volumes of 100% EtOH at −20° C. overnight. The precipitate was collected by centrifugation and was solubilized in 1 ml of Buffer C (4 M Gu-HCl, 20 mM Tris-HCl, pH 7.2). This solubilized pellet was used for chromatography on a calibrated gel filtration column (1.0× 50 cm column of Superose 6; Pharmacia) equilibrated in Buffer C (Flow=0.5 ml/min). Fractions were sampled for radioactivity, and those containing the $^{35}SO_4$ label that elutes with a molecular weight 70 kDa were pooled. The proteoglycan was precipitated with 100% EtOH as described above. The pellet was dissolved in 3 ml PBS, and dialyzed against 3×100 volumes of PBS. Each preparation of $^{35}$S-HSPG was confirmed to be 98% heparan sulfate by susceptibility to low pH nitrous acid degradation (Shiveley and Conrad, *Biochemistry* 15: 3932–3942 (1976)).

Measurement of Heparanase activity:

Heparanase activity from platelets or column fractions was detected by its ability to digest the 70 kDa $^{35}$S-HSPG to produce lower molecular weight products. not retained by a 30,000 MW cut-off membrane. Each digest contained 5–10 μl of sample to be assayed, $^{35}$S-HSPG (2000 cpm), 0.15 M NaCl, 0.03% human serum albumin, 10 μM MgCl$_2$, 10 μM CaCl$_2$, and 0.05 M Na acetate, pH 5.6 in a total volume of 300 μl. In the case of highly purified enzyme, the assay mixtures contained 2–5 ng of protein. Digests were carried out for 3 to 21 h. The presence of lower molecular weight radiolabeled products was detected by centrifugation through 30,000 MW-cutoff filters. The digests containing 2000 cpm of $^{35}$S-HSPG (>70 K) were centrifuged through 30,000 molecular weight cut-off filters (Millipore Ultrafree-MC 30,000 NMWL filter units). $^{35}$S-HSPG degradation was evident by the presence of radioactivity in the filtrate that passed through the 30 K membrane; this heparanase activity was expressed as the percent of total cpm <30,000 MW for a given digest. Analysis of heparan sulfate degradation by this method is quick and reproducible. One unit of heparanase activity is defined as that amount of enzyme which produces 1% of the total starting cpm that can pass through the 30,000 MW cut-off membrane in one hour. For pH optimum determination, the 0.1 M Na acetate buffer is replaced by 50 mM citrate, citrate-phosphate, or phosphate buffer at varying pH's.

Example 3

Preparation and Sequence Analysis of Peptides from Human Heparanase

Materials and Methods:

N-terminal amino acid sequencing of heparanase produced by this procedure was performed using a gas/liquid phase Protein Sequencer (Applied Biosystems Inc. Model 470). Phenylthiodantoin amino acids were resolved and quantitated by an on-line HPLC system (Model 120, Applied Biosystems Inc.) with data analysis on a Nelson Analytical System. The 65 kDa and 8 kDa polypeptides were both blocked at the N-terminus, presumably by PCA resulting from cyclization of Gln$_{23}$ of SEQ.ID.NO:2, while the 56 kDa protein gave a low yield sequence identical to residues 145–172 of the amino acid sequence given in SEQ ID NO:2. The identification of the 8 kDa chain was made by analysis of peptides derived therefrom by digestion with endoproteinase Lys C. Both Edman degradation and mass spectrometry were employed for this purpose. Electrospray MS revealed that the 8 kDa fragment corresponded exactly to the sequence of amino acid residues 23 through 96 of SEQ ID NO: 2.

Figure 6:
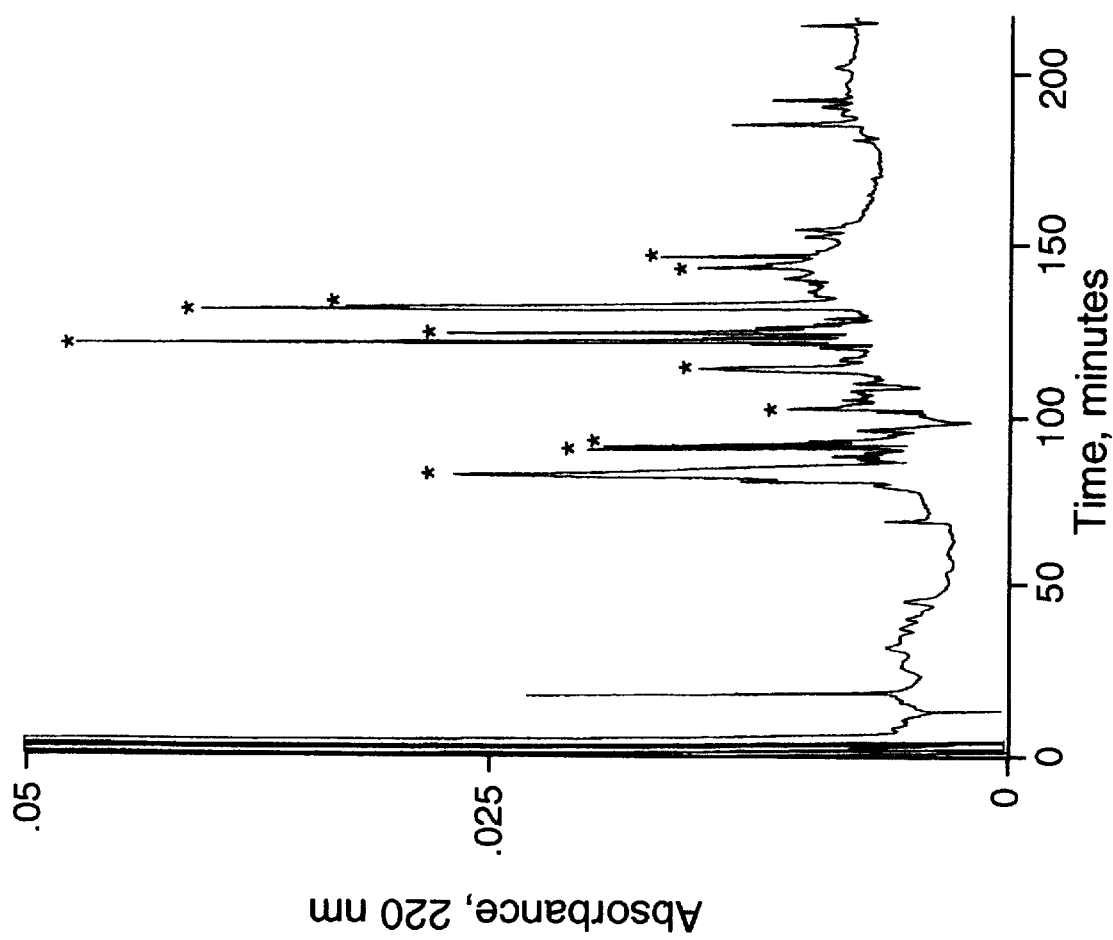
FIG. 6 is a graph depicting the results of separation of a mixture of endoLysC peptides derived from the 56 kDa protein using RP-HPLC. Starred peptides yielded sequence information which led to the discovery of an EST of human heparanase.

Results:

Automated Edman degradation of intact 56 kDa protein gave a sequence identical to residues 145–172 of the amino acid sequence given in SEQ ID NO: 2. The 8 kDa protein was refractive to Edman degradation because, as is shown below, it is blocked by cyclization of residue 23 of SEQ ID NO: 2 at the N-terminus (Q$_{23}$). Peptides were generated from the 56 kDa and 8 kDa chains of purified human platelet heparanase by cleavage of the proteins with trypsin, endoproteinase Lys C, and cyanogen bromide. Enzymatic digestion was performed at room temperature in 0.1 M Tris buffer, pH 7.5, with 1–5% by weight of the proteinase relative to heparanase. CNBr cleavage of the 56 kDa protein was performed in 70% formic acid with a large molar excess of reagent relative to protein. The amount of heparanase chain subjected to cleavage was from 2 to 5 μg. Peptides were resolved by RP-HPLC on a C18 Vydac column (1.0× 150 mm) equilibrated in 0.15% TFA. Elution of peptides was accomplished by a gradient of increasing acetonitrile concentration in 0.15% TFA from 0 to 100% over a period of 3 h at a flow rate of 0.1 ml/min. An example of the profile obtained for the endoLysC digest is shown in FIG. 6. Starred peptides, as well as a few select tryptic and CNBr peptides were sequenced. As is noted below in Example 4, these peptide sequences are contained withing the amino acid sequence deduced from the nucleotide sequence of a cDNA encoding human pre-proheparanase (see Example 4, below). FIG. 8 shows the sequence of 16 different peptides, and indicates the cleavage method used to generate each peptide. The numbered residues refer to the sequence shown in SEQ.ID.NO: 2.

The peptide sequences obtained as described above provided information that led to the identification of a corresponding EST DNA sequence in the Incyte database (access. # 1987692) which codes for amino acid residues 172–235 of SEQ ID NO: 2. Searches initiated with this EST led to identification of additional short segments of DNA sequence in public databases; these were em est3:HS349272 (residues 210–315 of SEQ ID NO: 2) and em est3:HS367274 (residues 236–339 of SEQ ID NO: 2). In no case were any of these ESTs associated with a known protein.

Example 4

Isolation and Sequencing of CDNA Encoding Human Heparanase

Synthesis of an Oligonucleotide Probe:

The first discovery of an EST from the human heparanase gene was made based upon a search with a nucleotide sequence corresponding to amino acid sequence of the endoLysC peptide having the sequence at amino acid residues 202 to 218 of SEQ ID NO: 2. This sequence was then used to screen private (Incyte) and public (EMBL-GENBANK) databases. EST3: HS367274 was found to contain the coding sequence for two of peptides, and several other of the sequenced protein peptides could now be placed relative to the gene sequence.

Two oligonucleotides were designed to amplify a 444 bp fragment whose sequence corresponds to that of nucleotides 569–1012 of SEQ ID NO: 1 using standard PCR methodology, where HUVEC cDNA was used as a template. The forward primer used was 5'-ATGCTCAGTTGCTCC-3' (nucleotide residues 569–583 of SEQ ID NO: 1), and the reverse primer used was 5'-CCGCCTCCATATGCAGAGCT-3' (SEQ ID NO: 3, which corresponds to the reverse complement of nucleotide residues 993–1012 of SEQ ID NO: 1). The PCR consisted of an initial denaturation step for 5 min at 95 C, 30 cycles of 30 sec denaturation at 95° C., 30 sec annealing at 60° C., and 30 sec extension at 72° C., followed by 5 min extension at 72° C. The PCR product was gel purified and cloned into the vector pNoTA/T7 (Primer PCR Cloner System, 5 Prime-3 Prime, Inc., Boulder, Colo.). The sequence of the insert was confirmed to correspond to that of EST3: H367274 by manual dideoxy-sequencing.

Library Screening:

A HUVEC cDNA library was purchased from Stratagene (Uni-ZAP™XR, Cat# 937223). The estimated titer of the library was $2.6 \times 10^{10}$ pfu/ml. Approximately $1 \times 10^6$ pfu were plated using XL1-Blue MRF' E.coli strain. A total of 20 plates were prepared, with each NZY 150 mm plate containing 50,000 pfu and 600 µl of $OD_{600}$ host cells, and 8 ml of top (0.7%) NZY agar. After overnight incubation at 37° C., plates were chilled for two hours and transferred into duplicate Hybond™-N (Amersham) filters for 2 min for the original and 4 min for the duplicate filters. Denaturation and fixation of the DNA transferred was accomplished by autoclaving the filters for 1 min at 100° C. using the setting for liquids.

After washing for 10 min in 2× SSC (20× SSC: 3.0M NaCl, 0.3M Na Citrate pH 7.0), the membranes were prehybridized at 65° C. for 1 hour in 200 ml of RapidHyb buffer (Amersham), using an air shaker at 150 RPM. The 444 base pair cDNA probe corresponding to nucleotides 569–1012 of SEQ ID NO: 1(25 ng) was labelled using I-$^{32}$P-dCTP and random primers, using the Prime-it$^R$II kit from Stratagene. Four reactions with a total of 200 ng labeled cDNA were used for hybridization in a 200 ml volume. Hybridization was at 65° C. for 2 hours. After hybridization, filters were washed as follows: two times for 15 min in 2× SSC-0.1% SDS at room temperature, followed by two times for 15 min in 1× SSC-0.1% SDS at 68° C. and two times for 10 min. in 1× SSC at room temperature.

After washing, excess liquid was removed by blotting on Whatman 3MM paper, and the filters were placed between two sheets of plastic wrap in a cassette with one intensifying screen. X-ray film (Hyperfilm, Amersham) was exposed for 18 to 48 hours. Duplicate positive signals were aligned with the corresponding plates and a 0.5 cm circle containing the putative clone was removed from the plate and placed in 1 ml of SM (0.1 M NaCl, 0.01 M $MgSO_4$, 50 mM Tris HCl pH7.5) with 20 µl chloroform. The stock containing the positive clones was subjected to several rounds of plating/hybridizing until a single isolated positive plaque could be obtained. These purified stocks were used for in vivo excision of the pBluescript phagemid with the insert from the Uni-ZAP vector, following the library's manufacturer's (Stratagene) protocol.

DNA Sequencing:

Heparanase cDNAs were sequenced directly using an AB1377 or ABI373A fluorescence-based sequencer (Perkin Elmer/Applied Biosystems Division, PE/ABD, Foster City, Calif.) and the ABI PRISM Ready Dye-Deoxy Terminator kit with Taq FS polymerase. Each ABI cycle sequencing reaction contained about 0.5 µg of plasmid DNA. Cycle-sequencing was performed using an initial denaturation at 98° C. for 1 min, followed by 50 cycles: 98 C for 30 sec, annealing at 50 C for 30 sec, and extension at 60 C for 4 min. Temperature cycles and times were controlled by a Perkin-Elmer 9600 thermocycler. Extension products were purified using Centriflex gel filtration (Advanced Genetic Technologies Corp., Gaithersburg, Md.). Each reaction product was loaded by pipette onto the column, which was then centrifuged in a swinging bucket centrifuge (Sorvall model RT6000B table top centrifuge) at 1500×g for 4 min at room temperature. Column-purified samples were dried under vacuum for about 40 min and then dissolved in 5 µl of a DNA loading solution (83% deionized formamide, 8.3 mM EDTA, and 1.6 mg/ml Blue Dextran). The samples were then heated to 90 C for three min and loaded into the gel sample wells for sequence analysis by the ABI377 sequencer. Sequence analysis was done by importing ABI373A files into the Sequencher program (Gene Codes, Ann Arbor, Mich.). Generally, sequence reads of 700 bp were obtained. Potential sequencing errors were minimized by obtaining sequence information from both DNA strands and by re-sequencing difficult areas using primers at different locations until all sequencing ambiguities were removed. The resulting sequence of the full-length cDNA is shown in SEQ.ID. NO: 1.

Example 5

Expression of Human Heparanase inE. coli

The entire polynucleotide molecule encoding any of the human heparanase polypeptides is amplified by PCR and cloned into an E. coli expression vector which contains a strong inducible promoter such as the PL or Tac promoters, upstream from a multiple cloning site. A purification handle such as a polyhistidine tail is introduced at the C-terminus of the protein, if not present in the vector. After ligation of insert and vector, the construct is transformed into suitable E. coli cells for expression. After induction, the cells are disrupted by sonication and the cell debris/insoluble fractions separated from the soluble fractions by centrifugation. The fractions obtained are analyzed by SDS PAGE to determine the localization of the recombinant protein. The recombinant protein is purified by standard methods and used for antibody production.

Example 6

Expression of Human Heparanase in Mammalian Cells

Expression of the 56 kDa Polypeptide of Human Platelet Heparanase in 293 Cells:

For expression of the 56 kDa polypeptide of human platelet heparanase in mammalian cells 293 (transformed primary embryonic kidney, human), a plasmid bearing the relevant heparanase coding sequence was prepared, using vector pSecTag2A (Invitrogen). The plasmid contains nucleotides 433 through 1590 of SEQ ID NO: 1. Vector pSecTag2A contains the murine IgK chain leader sequence for secretion, the C-myc epitope for detection of the recombinant protein with the antimyc antibody, a C-terminal polyhistidine for purification with nickel chelate chromatography, and a Zeocin resistant gene for selection of stable transfectants. The forward primer used for amplification of this heparanase cDNA was: 5'-GGCTACAAGCTT-GAAAAAGTTCAAGAACAGCACCTACTCA-3' (SEQ ID NO: 4) which contains a 5' extension of 12 nucleotides to introduce the HindIII cloning site and 27 nucleotides matching the heparanase sequence (nucleotides 433 through 459 of SEQ ID NO: 1). The reverse primer used for this construct was: 5'-GGCTGCTCGAGCGATGCAAGCAGCAACTTT-GGC-3' (SEQ ID NO: 5) which contains a 5' extension of 11 nucleotides to introduce an XhoI restriction site for cloning and 21 nucleotides corresponding to the reverse complement of the heparanase sequence from bases 1570 to 1590 of SEQ ID NO:1. The internal HindIII site (base 1249 through 1254 of SEQ ID NO: 1) was eliminated by site directed mutagenesis using the oligonucleotides: 5 '-GAAGGAAGCTG-CGAGTATACC-3' (SEQ ID NO:6) and 5'-GGTATACTC-GCAGCTTCCTTCC-3' (SEQ ID NO:7). The PCR conditions were as described in Example 4, using 55 C as the annealing temperature. The PCR product was gel purified and cloned into the HindIII-XhoI sites of the vector.

The DNA was purified using Qiagen chromatography columns and transfected into 293 cells using DOTAP transfection media (Boehringer Mannheim, Indianapolis, Ind.). Transiently transfected cells were tested for expression after 24 hours of transfection, using western blots probed with antiHis and anti-heparanase peptide antibodies. Permanently transfected cells were selected with Zeocin and propagated. Production of the recombinant protein was detected from both cells and media by western blots probed with antiHis, antiMyc or anti-heparanase peptide antibodies.

Expression of Pre-proheparanase, Proheparanase, and the 8 kDa Polypeptide of Human Platelet Heparanase in 293 Cells:

Expression of pre-proheparanase, proheparanase, and the 8 kDa polypeptide of human platelet heparanase in 293 cells may be accomplished essentially as described above for the 56 kDa polypeptide. For expression of pre-proheparanase, the cDNA molecule to be amplified and inserted into pSecTag2A is selected from the group consisting of (a) a polynucleotide encoding human pre-pro-heparanase polypeptide having the complete amino acid sequence of SEQ ID NO: 2 and (b) a polynucleotide molecule comprising nucleotides 1 through 1590 of SEQ ID NO: 1. For expression of proheparanase, the cDNA molecule to be amplified and inserted into pSecTag2A is selected from the group consisting of (a) a polynucleotide encoding human pro-heparanase polypeptide having the amino acid sequence at residues 23 through 530 of SEQ ID NO: 2 and (b) a polynucleotide molecule comprising nucleotides 69 through 1590 of SEQ ID NO: 1. For expression of the 8 kDa subunit of human heparanase, the cDNA molecule to be amplified and inserted into pSecTag2A is selected from the group consisting of a polynucleotide molecule encoding a polypeptide having the amino acid sequence at residues 23 through 96 of SEQ ID NO: 2, and (b) a polynucleotide molecule comprising residues 67 through 288 of SEQ ID NO: 1. Selection and preparation of primers suitable for PCR amplification of any of the above described polynucleotides is well within the skill of an ordinary artisan.

Expression of Human Platelet Heparanase in COS Cells:

For expression of the 56 kDa polypeptide of human platelet heparanase in COS7 cells, a polynucleotide molecule having the sequence given as nucleotides 433 through 1590 of SEQ ID NO: 1 was cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site. In addition, the plasmid contains the dhrf (dihydrofolate reductase) gene which provides selection in the presence of the drug methotrexane (MTX) for selection of stable transformants.

The forward primer used was 5'-GGCTATCTAGACT-GATGCTGCTGCTC-CTGG-3' (SEQ ID NO:8). The first 11 nucleotides of this primer constitute a 5' extension which introduces an XbaI restriction site for cloning, followed by 19 nucleotides which correspond to nucleotide residues 1–16 of the sequence given in SEQ ID NO: 1, preceded by the three nucleotides found immediately upstream of the first nucleotide of the sequence given in SEQ ID NO: 1. The reverse primer used was: 5'-GGTCTGTCGACTCAGATG-CAAGCAGCAACTT-3' (SEQ ID NO:9). This primer contains a 5'-extension of 11 n./leotides which introduces a SalI cloning site followed by 20 nucleotides which correspond to the reverse complement of bases 1574 to 1593 of the sequence given in SEQ ID NO: 1.

The PCR consisted of an initial denaturation step of 5 min at 95° C., 30 cycles of 30 sec denaturation at 95° C., 30 sec annealing at 58° C. and 30 sec extension at 72° C., followed by 5 min extension at 72° C. The PCR product was gel purified and ligated into the XbaI and SaII sites of vector p3-CI. This construct was transformed into E. coli cells for amplification and DNA purification. The DNA was purified with Qiagen chromatography columns and transfected into COS 7 cells using Lipofectamine reagent from BRL, following the manufacturer's protocols. Forty eight and 72 hours after transfection, the media and the cells were tested for recombinant protein expression.

Heparanase expressed from a COS cell culture may be purified by concentrating the cell-growth media to about 10 mg of protein/ml, and purifying the protein as described in Example 1. The purified heparanase is concentrated to 0.5 mg/ml in an Amicon concentrator fitted with a YM-10 membrane and stored at −80° C.

Expression of Pre-proheparanase, Proheparanase, and the 8 kDa Polypeptide of Human Platelet Heparanase in COS7 Cells:

Expression of pre-proheparanase, proheparanase, and the 8 kDa polypeptide of human platelet heparanase in COS7 cells may be accomplished essentially as described above for the 56 kDa polypeptide. For expression of pre-proheparanase, the cDNA molecule to be amplified and inserted into vector p3-CI is selected from the group consisting of (a) a polynucleotide encoding human pre-pro-heparanase polypeptide having the complete amino acid sequence of SEQ ID NO: 2 and (b) a polynucleotide molecule comprising nucleotides 1 through 1590 of SEQ ID NO:1. For expression of proheparanase, the cDNA molecule to be amplified and inserted into vector p3-CI is selected from the group consisting of (a) a polynucleotide encoding human pro-heparanase polypeptide having the amino acid sequence at residues 23 through 530 of SEQ ID NO: 2 and (b) a polynucleotide molecule comprising nucleotides 67 through 1590 of SEQ ID NO: 1. For expression of the 8 kDa subunit of human heparanase, the cDNA molecule to be amplified and inserted into vector p3-CI is selected from the group consisting of a polynucleotide molecule encoding a polypeptide having the amino acid sequence at residues 23 through 96 of SEQ ID NO: 2, and (b) a polynucleotide molecule comprising residues 67 through 288 of SEQ ID NO: 1. Selection and preparation of primers suitable for PCR amplification of any of the above described polynucleotides is well within the skill of an ordinary artisan.

Example 7

Expression of Human Heparanase in Insect Cells

Expression of the 56 kDa Polypeptide of Human Platelet Heparanase in a Baculovirus System:

For expression of the 56 kDa polypeptide of human platelet heparanase in a baculovirus system, a polynucleotide molecule having the sequence given as nucleotides 433 through 1590 of SEQ ID NO: 1 was amplified by PCR. The forward primer used was: 5'-GGATCATATGCAAAAAGTTCAAGAACAGCACCT-AC-3' (SEQ ID NO:10). The first 11 nucleotides of this primer constitute a 5' extension which adds the NdeI cloning site, followed by followed by 24 nucleotides which correspond to nucleotide residues 433 through 456 of the sequence given in SEQ ID NO: 1. The reverse primer was 5'-GGCTCGGTACCTCAGATGCAAGCAGC-AACTTTGGC-3' (SEQ ID NO:11). The first 11 nucleotides of this primer constitute a 5' extension which introduces the KpnI cloning site, followed by followed by 24 nucleotides which correspond to the reverse complement of nucleotide residues 1570 through 1593 of the sequence given in SEQ ID NO: 1.

An internal NdeI site was eliminated by site-directed mutagenesis using oligonucleotides. The forward primer was 5'-AGCTCTGCATACGGAGGCGGA-3' (SEQ ID NO: 12) and the reverse primer was 5'-TCCGCCTCCGTATGCAGAGCT-3' (SEQ ID NO:13).

The PCR product was gel purified, digested with NdeI and KpnI, and cloned into the corresponding sites of vector pACHTL-A (Pharmingen, San Diego, Calif.). The pAcHTL expression vector contains the strong polyhedrin promoter of the *Autographa californica* nuclear polyhedrosis virus (AcMNPV), and a 6XHis tag upstream from the multiple cloning site. A protein kinase site for phosphorylation and a thrombin site for excision of the recombinant protein precede the multiple cloning site. Of course, many other baculovirus vectors could be used in place of pAcHTL-A, such as pAc373, pVL941 and pAcIM1. Other suitable vectors for the expression of human heparanase polypeptides may be used, provided that the vector construct includes appropriately located signals for transcription, translation, and trafficking, such as an in-frame AUG and a signal peptide, as required. Such vectors are described in Luckow et al., Virology 170:31–39, among others.

The virus was grown and isolated using standard baculovirus expression methods, such as those described in Summers et al. (*A Manual of Methods for Baculovirus Vectors and Insect Cell Culture Procedures*, Texas Agricultural Experimental Station Bulletin No. 1555 (1987)). In a preferred embodiment, pAcHLT-A containing the human heparanase gene is introduced into baculovirus using the "BaculoGold" transfection kit (Pharmingen, San Diego, Calif.) using methods established by the manufacturer. Individual virus isolates were analyzed for protein production by radiolabeling infected cells with $^{35}$S-methionine at 24 hours post infection. Infected cells were harvested at 48 hours post infection, and the labeled proteins are visualized by SDS-PAGE. Viruses exhibiting high expression levels may be isolated and used for scaled up expression.

Expression of Pre-proheparanase, Proheparanase, and the 8 kDa Polypeptide of Human Platelet Heparanase in a Baculovirus System:

Expression of pre-proheparanase, proheparanase, and the 8 kDa polypeptide of human platelet heparanase in a baculovirus system may be accomplished essentially as described above for the 56 kDa polypeptide. For expression of pre-proheparanase, the cDNA molecule to be amplified and inserted into vector pAcHTL-A is selected from the group consisting of (a) a polynucleotide encoding human pre-proheparanase polypeptide having the complete amino acid sequence of SEQ ID NO:2 and (b) a polynucleotide molecule comprising nucleotides 1 through 1590 of SEQ ID NO:1. For expression of proheparanase, the cDNA molecule to be amplified and inserted into vector pAcHTL-A is selected from the group consisting of (a) a polynucleotide encoding human pro-heparanase polypeptide having the amino acid sequence at residues 23 through 530 of SEQ ID NO:2 and (b) a polynucleotide molecule comprising nucleotides 67 through 1590 of SEQ ID NO:1. For expression of the 8 kDa subunit of human heparanase, the cDNA molecule to be amplified and inserted into vector pAcHLT-A is selected from the group consisting of a polynucleotide molecule encoding a polypeptide having the amino acid sequence at residues 23 through 96 of SEQ ID NO:2, and (b) a polynucleotide molecule comprising residues 67 through 288 of SEQ ID NO:1. Selection and preparation of primers suitable for PCR amplification of any of the above described polynucleotides is well within the skill of an ordinary artisan.

Expression of the 56 kDa Polypeptide of Human Platelet Heparanase in Sf9 Insect Cells:

For expression of the 56 kDa polypeptide of human platelet heparanase in a Sf9 cells, a polynucleotide molecule having the sequence given as nucleotides 433 through 1590 of SEQ ID NO:1 was amplified by PCR using the primers and methods described above for baculovirus expression. The heparanase cDNA was cloned into vector pAcHLT-A (Pharmingen) for expression in Sf9 insect. The insert was cloned into the NdeI and KpnI sites, after elimination of an internal NdeI site (using the same primers described above for expression in baculovirus). DNA was purified with Qiagen chromatography columns and expressed in Sf9 cells. Preliminary Western blot experiments from non purified plaques were tested for the presence of the recombinant protein of the expected size which reacted with the heparanase specific antibody. These results were confirmed after further purification and expression optimization in HiG5 cells.

Expression of Pre-proheparanase, Proheparanase, and the 8 kDa Polypeptide of Human Platelet Heparanase in Sf9 Cells:

Expression of pre-proheparanase, proheparanase, and the 8 kDa polypeptide of human platelet heparanase in Sf9 cells may be accomplished essentially as described above for the 56 kDa polypeptide. For expression of pre-proheparanase, the cDNA molecule to be amplified and inserted into vector pAcHLT-A is selected from the group consisting of (a) a polynucleotide encoding human pre-pro-heparanase polypeptide having the complete amino acid sequence of SEQ ID NO:2 and (b) a polynucleotide molecule comprising nucleotides 1 through 1590 of SEQ ID NO:1. For expression of proheparanase, the cDNA molecule to be amplified and inserted into vector pAcHTL-A is selected from the group consisting of (a) a polynucleotide encoding human pro-heparanase polypeptide having the amino acid sequence at residues 23 through 530 of SEQ ID NO:2 and (b) a polynucleotide molecule comprising nucleotides 67 through 1590 of SEQ ID NO:1. For expression of the 8 kDa subunit of human heparanase, the CDNA molecule to be amplified and inserted into vector pAcHLT-A is selected from the group consisting of a polynucleotide molecule encoding a polypeptide having the amino acid sequence at residues 23 through 96 of SEQ ID NO:2, and (b) a polynucleotide molecule comprising residues 67 through 288 of SEQ ID NO:2. Selection and preparation of primers suitable for PCR

Example 8

Preparation of Antibodies Against Human Heparanase

Preparation of Peptide Immutnogen:

Peptides for raising antibodies were synthesized according to standard solid phase synthetic procedures, in which a final Cys, or Gly-Gly-Cys sequence was added to the C-terminus of a chosen human heparanase peptide. The C-terminal Cys residue was for the purpose of conjugation of the peptide to the keyhole limpet hemocyanin (KLH) carrier protein. Two peptides were chosen for this purpose; the first corresponds to residues 326–337 of the heparanase sequence given in SEQ ID NO:2 (to which a C-terminal Cys residue was added for conjugation), and the second corresponds to residues 260–277 of the amino acid sequence given in SEQ ID NO:2 (to which the C-terminal sequence Gly-Gly-Cys was added for conjugation). These peptides were produced by stepwise solid phase peptide synthesis on an Applied Biosystems 430A Peptide Synthesizer. 9-Fluoroenylmethyloxycarbonyl (Fmoc) was used as the $N^I$ amino protecting group, and temporary side-chain protectin groups were as follows: Arg (Pmc), Asn (Trt), Asp (OtBu), Gln (Trt), Glu (OtBu), His (Trt), Lys (Boc), Ser (tBu), Thr (tBu). Each residue was single coupled using a HBTU/NMP protocol and capped with acetic anhydride before the next synthesis cycle. Alter removal of the N-terminal Fmoc group, temporary side-chain protecting groups were removed and the peptide cleaved from the resin by treatment with 95% TFA/5% scavengers (ethyl methyl sulfide/anisole/1,2-ethanedithiol, 1:3:1) for two hours at room temperature. The crude peptides were precipitated from the cleavage solution with cold diethyl ether. The precipitated peptide was collected on a sintered glass funnel, washed with diethyl ether, dissolved in dilute acetic acid, evaporated to dryness under reduced pressure, and the residue was redissolved and lyophillized from glacial acetic acid. The crude peptides were purified by preparative reverse phase chromatography on a Phenomenex C-18 column (22.5×250 mm) using a water/acetonitrile gradient, each phase containing 0.1% trifluoroacetic acid (TFA). Pure fractions, as determined by analytical HPLC, were pooled, the acetonitrile was evaporated under reduced pressure, and the aqueous solution was lyophillized. The purified peptides were characterized by time of flight or FAB mass spectroscopy. The synthetic peptides were conjugated to KLH utilizing a maleimide-activated carrier protein (Pierce Chemical Co. Cat. No. 77106).

Antisera Production:

Conjugated peptides (1.5 mg) were injected into a rabbit using Freund's complete adjuvant. The antisera were collected 5 weeks after initial immunization, with subsequent collections at 3-week intervals. The 3rd (last) bleed gave highest titers of antibody as measured in a standard ELISA against the peptide antigen plated out in a 96-well microtiter plate (donkey anti-rabbit HRP-labeled secondary antibody). The antisera react with peptide conjugated to ovalbumin as detected by western blotting of SDS-PAGE gels. The antisera also recognize both the 65 kDa and the 56 kDa heparanases, as evidenced by their successful application in western blots but, as expected, did not recognize the 8 kDa polypeptide from human platelets. The antisera also gave positive results for heparanase partially purified from human neutrophils, suggesting an identical enzyme in these leucocytes. Accordingly, these antibodies may be used to monitor the course of purification of the heparanase species from human tissues.

Example 9

Identification of Agents Capable of Inhibiting Heparanase Activity

The purified heparanase of the present invention, both recombinantly produced human heparanase and heparanase isolated from human platelet cells, allows for the convenient selection of compounds having anti-heparanase activity, i.e., inhibitors of heparanase activity (IHA), by measuring inhibition of heparanase activity. Inhibition of heparanase activity can be measured by blocking heparanase-mediated release of radioactive fragments from in vivo radiolabeled (HSPG)/heparin, as seen by the failure to produce breakdown fragments of a size that will pass through a 30,000 MW cut-off membrane. In this experiment, the ligand is radiolabeled to high specific activity by intraperitoneal injection of 0.5 mCi of $^{35}$S-sulfate into C57 mice bearing a 1–2 cm basement membrane tumor (EHS; Engelbreth, Holm, Swarm tumor). The tumor was harvested after 16 hours and the HSPG extracted in 4 volumes of 6 M urea, 20 mM Tris, pH 6.8, protease inhibitors, 0.15 M NaCl and 0.5% triton X-100. The urea extract was chromatographed on an anion exchange column and the HSPG eluted in a linear gradient of NaCl. The radiolabeled HSPG was exchanged into a solution of 4.0 M guanidine-HCl, 20 mM Tris, pH 7.4 and applied to a size exclusion column. The HSPG peak was pooled and exchanged into 0.15 mM NaCl and 20 mM Tris pH 7.4.

For purposes of high throughput screening, it is desirable to exploit assays that can be conducted in a 96-well microtiter plate format. In this case, the protein component of chromatographically purified $^{35}$S-HSPG is digested enzymatically by any non-specific enzyme, such as papain, to give free N-terminal amino groups. The [$^{35}$ SO$_4$] heparan sulfated peptides are then coupled to cyanogen bromide activated Sepharose-6B (Pharmacia Biotech) according to manufacturer's instructions. The $^{35}$S-Heparan sulfate-Sepharose 6B is resuspended in: 0.15 M NaCl, 0.03% human serum albumin, 10 $\mu$M MgCl$_2$, 10 $\mu$M CaCl$_2$, antiproteolytic agents (1 $\mu$g/ml leupeptin, 2 $\mu$g/ml antipain, 10 $\mu$g/ml benzamidine, 10 units/ml aprotinin, 1 $\mu$g/ml chymostatin, and 1 $\mu$g/ml pepstatin), and 0.05 M Na acetate, pH 5.6 and 5,000 cpm, in a total volume of 200 $\mu$l. This solution is then aliquoted into each well of a 96 well plate, which contains in each well a different test agent. Heparanase (5 units) is added to each well, and the digestion is allowed to proceed overnight (16 h) at 37° C.

The digested products are then separated from the supernatant by centrifugation of the 96 well plate through a 30,000 MW cut-off membrane. The supernatant, containing cleaved heparan sulfate, is decanted and quantitated by scintillation counting. Agents which alter the activity of the heparanase may thus be identified by comparing the amount of cleaved heparan sulfate in each test agent well with that in a control well lacking a test agent.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

What is claimed is:

1. An isolated human heparanase polypeptide comprising an amino acid sequence selected from the group consisting of:
   (a) an amino acid sequence of a human pre-proheparanase polypeptide having the complete amino acid sequence of SEQ ID NO:2;
   (b) an amino acid sequence of a human proheparanase polypeptide having the amino acid sequence at residues 23 through 530 of SEQ ID NO:2;
   (c) an amino acid sequence of the 8 kDa subunit of human heparanase having amino acid sequence at residues 23 through 96 of SEQ ID NO:2; and
   (d) an amino acid sequence of the 56 kDa subunit of human heparanase having the amino acid sequence at residues 145 through 530 of SEQ ID NO:2.

2. The isolated human heparanase polypeptide of claim 1, wherein said polypeptide comprises an amino acid sequence of the 8 kDa subunit of human heparanase having the amino acid sequence at residues 23 through 96 of SEQ ID NO:2.

3. A human heparanase enzyme comprising
   (a) an isolated human heparanase polypeptide comprising the amino acid sequence at residues 145 through 530 of SEQ ID NO:2; and
   (b) an isolated human heparanase polypeptide comprising the amino acid sequence at residues 23 through 96 of SEQ ID NO:2.

4. The human heparanase enzyme of claim 3, wherein
   (a) the isolated human heparanase polypeptide of 15(a) is expressed from an isolated nucleic acid molecule comprising a polynucleotide having the nucleotide sequence at 433 through 1590 of SEQ ID NO:1; and
   (b) the isolated human heparanase polypeptide of 15(b) is expressed from an isolated nucleic acid molecule comprising a polynucleotide having the nucleotide sequence at residues 67 through 288 of SEQ ID NO:1.

5. A human heparanase enzyme comprising
   (a) an isolated human heparanase polypeptide that is encoded by an isolated nucleic acid molecule comprising a polynucleotide having a sequence at least 95% identical to a polynucleotide having the nucleotide sequence at residues 433 through 1590 of SEQ ID NO:1; and
   (b) an isolated human heparanase polypeptide that is encoded by an isolated nucleic acid molecule comprising a polynucleotide having a sequence at least 95% identical to a polynucleotide having the nucleotide sequence at residues 67 through 288 of SEQ ID NO:1.

6. A method for the identification of an agent that alters heparanase activity, said method comprising:
   (a) determining the activity of the isolated human heparanase enzyme of claim 3, 4, or 5
      (i) in the presence of a test agent; and
      (ii) in the absence of said test agent; and
   (b) comparing the heparanase activity determined in step (a)(i) to the heparanase activity determined in step (a)(ii); whereby a change in heparanase activity in sample (a)(i) has compared to sample (a)(ii) indicates that said agent alters the activity of said human heparanase.

7. The method of claim 6, wherein said agent increases heparanase activity.

8. The method of claim 6, wherein said agent inhibits heparanase activity.

9. The method of claim 6, wherein the determination of heparanase activity is made by measuring the amount of radiolabeled heparin/heparan sulfate that is digested by said human heparanase enzyme.

10. An isolated human heparanase wherein said polypeptide comprises an amino acid sequence of the 56 kDa subunit of human heparanase polypeptide having the amino acid sequence at residues 145 through 530 of SEQ ID NO:2.

* * * * *

UNITED STATES PATENT AND TRADEMARK OFFICE
CERTIFICATE OF CORRECTION

PATENT NO.   : 6,387,643 B1
DATED        : May 14, 2002
INVENTOR(S)  : Heinrikson et al.

It is certified that error appears in the above-identified patent and that said Letters Patent is hereby corrected as shown below:

<u>Column 46,</u>
Line 44, -- polypeptide -- should be inserted between the words "heparanase" and "wherein".

Signed and Sealed this

Ninth Day of July, 2002

Attest:

JAMES E. ROGAN
*Attesting Officer*   *Director of the United States Patent and Trademark Office*